United States Patent
Nikolskiy et al.

(10) Patent No.: US 7,428,481 B2
(45) Date of Patent: *Sep. 23, 2008

(54) EFFICIENT DATA REPRESENTATION OF TEETH MODEL

(75) Inventors: Sergey Nikolskiy, Moscow (RU); Elena Pavloskaia, San Francisco, CA (US); Huafeng Wen, Redwood Shores, CA (US)

(73) Assignee: Align Technology, Inc., Santa Clara, CA (US)

( * ) Notice: Subject to any disclaimer, the term of this patent is extended or adjusted under 35 U.S.C. 154(b) by 127 days.

This patent is subject to a terminal disclaimer.

(21) Appl. No.: 10/359,998

(22) Filed: Feb. 7, 2003

(65) Prior Publication Data

US 2003/0139834 A1    Jul. 24, 2003

Related U.S. Application Data

(63) Continuation of application No. 10/359,998, filed on Feb. 7, 2003, which is a continuation of application No. 09/576,721, filed on May 23, 2000, now Pat. No. 6,633,789, which is a continuation-in-part of application No. 09/506,419, filed on Feb. 17, 2000, now Pat. No. 6,463,344.

(51) Int. Cl.
    *G06G 7/48* (2006.01)

(52) U.S. Cl. .................. 703/6; 703/1; 703/2; 703/7; 29/896.1

(58) Field of Classification Search .................. 700/97, 700/98, 118–120, 163; 433/2, 24; 703/2, 703/7, 1, 6; 382/154, 128; 345/419, 420; 29/896.1, 896.11

See application file for complete search history.

(56) References Cited

U.S. PATENT DOCUMENTS

| | | | |
|---|---|---|---|
| 2,467,432 | A | 4/1949 | Kesling |
| 3,407,500 | A | 10/1968 | Kesling |
| 3,600,808 | A | 8/1971 | Reeve |
| 3,660,900 | A | 5/1972 | Andrews |
| 3,683,502 | A | 8/1972 | Wallshein |
| 3,738,005 | A | 6/1973 | Cohen |

(Continued)

FOREIGN PATENT DOCUMENTS

AU    3031677    5/1979

(Continued)

OTHER PUBLICATIONS

Bourke, Paul. "Coordinate System Transformation". Jun. 1996. http://local.wasp.uwa.edu.au/~pbourke/projection/coords/.*

(Continued)

*Primary Examiner*—Paul L Rodriguez
*Assistant Examiner*—Jason Proctor
(74) *Attorney, Agent, or Firm*—Tonwsend and Townsend and Crew LLP

(57) ABSTRACT

A computer-implemented method generates a computer model of one or more teeth by receiving as input a digital data set of meshes representing the teeth; selecting a curved coordinate system with mappings to and from a 3D space; and generating a function in the curved coordinate system to represent each tooth.

18 Claims, 13 Drawing Sheets

U.S. PATENT DOCUMENTS

| | | | |
|---|---|---|---|
| 3,860,803 A | 1/1975 | Levine | |
| 3,916,526 A | 11/1975 | Schudy | |
| 3,922,786 A | 12/1975 | Lavin | |
| 3,950,851 A | 4/1976 | Bergersen | |
| 3,983,628 A | 10/1976 | Acevedo | |
| 4,014,096 A | 3/1977 | Dellinger | |
| 4,195,046 A | 3/1980 | Kesling | |
| 4,253,828 A | 3/1981 | Coles et al. | |
| 4,324,546 A | 4/1982 | Heitlinger et al. | |
| 4,324,547 A | 4/1982 | Arcan et al. | |
| 4,348,178 A | 9/1982 | Kurz | |
| 4,478,580 A | 10/1984 | Barrut | |
| 4,500,294 A | 2/1985 | Lewis | |
| 4,504,225 A | 3/1985 | Yoshii | |
| 4,505,673 A | 3/1985 | Yoshii | |
| 4,526,540 A | 7/1985 | Dellinger | |
| 4,575,330 A | 3/1986 | Hull | |
| 4,575,805 A | 3/1986 | Moermann et al. | |
| 4,591,341 A | 5/1986 | Andrews | |
| 4,609,349 A | 9/1986 | Cain | |
| 4,611,288 A | 9/1986 | Duret et al. | |
| 4,656,860 A | 4/1987 | Orthuber et al. | |
| 4,663,720 A | 5/1987 | Duret et al. | |
| 4,664,626 A | 5/1987 | Kesling | |
| 4,676,747 A | 6/1987 | Kesling | |
| 4,742,464 A | 5/1988 | Duret et al. | |
| 4,755,139 A | 7/1988 | Abbatte et al. | |
| 4,763,791 A | 8/1988 | Halverson et al. | |
| 4,793,803 A | 12/1988 | Martz | |
| 4,798,534 A | 1/1989 | Breads | |
| 4,836,778 A | 6/1989 | Baumrind et al. | |
| 4,837,732 A | 6/1989 | Brandestini et al. | |
| 4,850,864 A | 7/1989 | Diamond | |
| 4,850,865 A | 7/1989 | Napolitano | |
| 4,856,991 A | 8/1989 | Breads et al. | |
| 4,877,398 A | 10/1989 | Kesling | |
| 4,880,380 A | 11/1989 | Martz | |
| 4,889,238 A | 12/1989 | Batchelor | |
| 4,890,608 A | 1/1990 | Steer | |
| 4,935,635 A | 6/1990 | O'Harra | |
| 4,936,862 A | 6/1990 | Walker et al. | |
| 4,937,928 A | 7/1990 | van der Zel | |
| 4,941,826 A | 7/1990 | Loran et al. | |
| 4,964,770 A | 10/1990 | Steinbichler et al. | |
| 4,975,052 A | 12/1990 | Spencer et al. | |
| 4,983,334 A | 1/1991 | Adell | |
| 5,011,405 A | 4/1991 | Lemchen | |
| 5,017,133 A | 5/1991 | Miura | |
| 5,027,281 A | 6/1991 | Rekow et al. | |
| 5,035,613 A | 7/1991 | Breads et al. | |
| 5,055,039 A | 10/1991 | Abbatte et al. | |
| 5,059,118 A | 10/1991 | Breads et al. | |
| 5,100,316 A | 3/1992 | Wildman | |
| 5,107,444 A * | 4/1992 | Wu | 345/419 |
| 5,121,333 A | 6/1992 | Riley et al. | |
| 5,125,832 A | 6/1992 | Kesling | |
| 5,128,870 A | 7/1992 | Erdman et al. | |
| 5,130,064 A | 7/1992 | Smalley | |
| 5,131,843 A | 7/1992 | Hilgers et al. | |
| 5,131,844 A | 7/1992 | Marinaccio et al. | |
| 5,139,419 A | 8/1992 | Andreiko et al. | |
| 5,145,364 A | 9/1992 | Martz et al. | |
| 5,176,517 A | 1/1993 | Truax | |
| 5,184,306 A | 2/1993 | Erdman et al. | |
| 5,186,623 A | 2/1993 | Breads et al. | |
| 5,257,203 A | 10/1993 | Riley et al. | |
| 5,273,429 A | 12/1993 | Rekow et al. | |
| 5,278,756 A | 1/1994 | Lemchen et al. | |
| 5,328,362 A | 7/1994 | Watson et al. | |
| 5,338,198 A | 8/1994 | Wu et al. | |
| 5,340,309 A | 8/1994 | Robertson | |
| 5,342,202 A | 8/1994 | Deshayes | |
| 5,368,478 A | 11/1994 | Andreiko et al. | |
| 5,382,164 A | 1/1995 | Stern | |
| 5,395,238 A | 3/1995 | Andreiko et al. | |
| 5,431,562 A | 7/1995 | Andreiko et al. | |
| 5,440,326 A | 8/1995 | Quinn | |
| 5,440,496 A | 8/1995 | Andersson et al. | |
| 5,447,432 A | 9/1995 | Andreiko et al. | |
| 5,452,219 A | 9/1995 | Dehoff et al. | |
| 5,454,717 A | 10/1995 | Andreiko et al. | |
| 5,456,600 A | 10/1995 | Andreiko et al. | |
| 5,474,448 A | 12/1995 | Andreiko et al. | |
| RE35,169 E | 3/1996 | Lemchen et al. | |
| 5,518,397 A | 5/1996 | Andreiko et al. | |
| 5,528,735 A | 6/1996 | Strasnick et al. | |
| 5,533,895 A | 7/1996 | Andreiko et al. | |
| 5,542,842 A | 8/1996 | Andreiko et al. | |
| 5,549,476 A | 8/1996 | Stern | |
| 5,562,448 A | 10/1996 | Mushabac | |
| 5,587,912 A | 12/1996 | Andersson et al. | |
| 5,590,248 A | 12/1996 | Zarge et al. | |
| 5,605,459 A | 2/1997 | Kuroda et al. | |
| 5,607,305 A | 3/1997 | Andersson et al. | |
| 5,614,075 A | 3/1997 | Andre | |
| 5,621,648 A | 4/1997 | Crump | |
| 5,645,420 A | 7/1997 | Bergersen | |
| 5,645,421 A | 7/1997 | Slootsky | |
| 5,655,653 A | 8/1997 | Chester | |
| 5,683,243 A | 11/1997 | Andreiko et al. | |
| 5,692,894 A | 12/1997 | Schwartz et al. | |
| 5,725,376 A | 3/1998 | Poirier | |
| 5,725,378 A | 3/1998 | Wang | |
| 5,733,126 A | 3/1998 | Andersson et al. | |
| 5,740,267 A | 4/1998 | Echerer et al. | |
| 5,742,700 A | 4/1998 | Yoon et al. | |
| 5,799,100 A | 8/1998 | Clarke et al. | |
| 5,800,174 A | 9/1998 | Andersson | |
| 5,823,778 A | 10/1998 | Schmitt et al. | |
| 5,848,115 A | 12/1998 | Little et al. | |
| 5,857,853 A | 1/1999 | van Nifterick et al. | |
| 5,866,058 A | 2/1999 | Batchelder et al. | |
| 5,879,158 A | 3/1999 | Doyle et al. | |
| 5,880,961 A | 3/1999 | Crump | |
| 5,880,962 A | 3/1999 | Andersson et al. | |
| 5,882,192 A | 3/1999 | Bergersen | |
| 6,054,990 A | 5/1999 | Stewart et al. | |
| 5,934,288 A | 8/1999 | Avila et al. | |
| 5,957,686 A | 9/1999 | Anthony | |
| 5,964,587 A | 10/1999 | Sato | |
| 5,971,754 A | 10/1999 | Sondhi et al. | |
| 5,975,893 A | 11/1999 | Chishti et al. | |
| 6,015,289 A | 1/2000 | Andreiko et al. | |
| 6,044,170 A * | 3/2000 | Migdal et al. | 382/154 |
| 6,044,309 A | 3/2000 | Honda | |
| 6,049,743 A | 4/2000 | Baba | |
| 6,062,861 A | 5/2000 | Andersson | |
| 6,068,482 A | 5/2000 | Snow | |
| 6,099,314 A | 8/2000 | Kopelman et al. | |
| 6,123,544 A | 9/2000 | Cleary | |
| 6,151,404 A | 11/2000 | Pieper | |
| 6,152,731 A | 11/2000 | Jordan et al. | |
| 6,183,248 B1 | 2/2001 | Chishti et al. | |
| 6,190,165 B1 | 2/2001 | Andreiko et al. | |
| 6,205,243 B1 | 3/2001 | Migdal et al. | |
| 6,210,162 B1 | 4/2001 | Chishti et al. | |
| 6,212,442 B1 | 4/2001 | Andersson et al. | |
| 6,217,325 B1 | 4/2001 | Chishti et al. | |
| 6,217,334 B1 | 4/2001 | Hultgren | |
| 6,227,850 B1 * | 5/2001 | Chishti et al. | 433/24 |
| 6,244,861 B1 | 6/2001 | Andreiko et al. | |
| 6,250,918 B1 | 6/2001 | Sachdeva et al. | |
| 6,260,000 B1 * | 7/2001 | Karasaki et al. | 702/155 |
| 6,300,958 B1 * | 10/2001 | Mallet | 345/442 |

| | | |
|---|---|---|
| 6,309,215 B1 | 10/2001 | Phan et al. |
| 6,315,553 B1 | 11/2001 | Sachdeva et al. |
| 6,318,994 B1 | 11/2001 | Chishti et al. |
| 6,322,359 B1 | 11/2001 | Jordan et al. |
| 6,350,119 B1 | 2/2002 | Jordan et al. |
| 6,350,120 B1 | 2/2002 | Sachdeva et al. |
| 6,369,815 B1 * | 4/2002 | Celniker et al. ............ 345/420 |
| 6,371,761 B1 | 4/2002 | Cheang et al. |
| 6,382,975 B1 | 5/2002 | Poirier |
| 6,398,548 B1 | 6/2002 | Muhammad et al. |
| 6,402,707 B1 | 6/2002 | Ernst |
| 6,409,504 B1 | 6/2002 | Jones et al. |
| 6,431,870 B1 | 8/2002 | Sachdeva |
| 6,463,344 B1 | 10/2002 | Pavloskaia et al. |
| 6,463,351 B1 | 10/2002 | Clynch |
| 6,471,512 B1 | 10/2002 | Sachdeva |
| 6,482,298 B1 | 11/2002 | Bhatnagar |
| 6,512,994 B1 * | 1/2003 | Sachdeva .................... 702/167 |
| 6,514,074 B1 | 2/2003 | Chishti et al. |
| 6,524,101 B1 | 2/2003 | Phan et al. |
| 6,540,512 B1 * | 4/2003 | Sachdeva et al. ............. 433/24 |
| 6,545,678 B1 * | 4/2003 | Ohazama ................... 345/427 |
| 6,554,611 B2 | 4/2003 | Chishti et al. |
| 6,558,162 B1 | 5/2003 | Porter et al. |
| 6,572,372 B1 | 6/2003 | Phan et al. |
| 6,602,070 B2 | 8/2003 | Miller et al. |
| 6,629,840 B2 | 10/2003 | Chishti et al. |
| 6,633,789 B1 | 10/2003 | Nikolskiy et al. |
| 6,665,570 B2 | 12/2003 | Pavloskaia et al. |
| 6,688,886 B2 | 2/2004 | Hughes et al. |
| 6,705,863 B2 | 3/2004 | Phan et al. |
| 6,722,880 B2 | 4/2004 | Chishti et al. |
| 2002/0006597 A1 | 1/2002 | Andreiko et al. |
| 2002/0018981 A1 | 2/2002 | Andersson et al. |
| 2002/0055800 A1 | 5/2002 | Nikolskiy et al. |
| 2003/0009252 A1 | 1/2003 | Pavlovskaia et al. |
| 2003/0139834 A1 | 7/2003 | Nikolskiy et al. |
| 2003/0156111 A1 * | 8/2003 | Joshi et al. .................. 345/420 |
| 2003/0224311 A1 | 12/2003 | Cronauer |
| 2004/0128010 A1 | 7/2004 | Pavlovskala et al. |
| 2004/0189633 A1 * | 9/2004 | Sederberg .................. 345/418 |
| 2005/0018885 A1 * | 1/2005 | Chen et al. ................. 382/128 |
| 2005/0055118 A1 | 3/2005 | Nikolskiy et al. |

FOREIGN PATENT DOCUMENTS

| | | |
|---|---|---|
| AU | 51702 | 7/1981 |
| AU | 5598894 | 6/1994 |
| CA | 1121955 | 4/1982 |
| DE | 2749802 | 5/1978 |
| DE | 69327661 | 7/2000 |
| EP | 091876 A1 | 10/1983 |
| EP | 0091876 A1 | 10/1983 |
| EP | 0731673 B1 | 9/1988 |
| EP | 299490 A2 | 1/1989 |
| EP | 0299490 A2 | 1/1989 |
| EP | 376873 A2 | 7/1990 |
| EP | 0376873 A2 | 7/1990 |
| EP | 490848 B1 | 6/1992 |
| EP | 0490848 B1 | 6/1992 |
| EP | 0667753 | 8/1995 |
| EP | 774933 B1 | 5/1997 |
| EP | 0774933 B1 | 5/1997 |
| EP | 0541500 A1 | 6/1998 |
| EP | 541500 A1 | 6/1998 |
| EP | 731673 B1 | 9/1998 |
| ES | 463897 | 1/1980 |
| FR | 2369828 A1 | 6/1978 |
| FR | 2652256 A1 | 3/1991 |
| GB | 1550777 | 8/1979 |
| JP | 53-058191 | 5/1978 |
| JP | 04-028359 | 1/1992 |
| JP | 08-508174 | 9/1996 |
| WO | WO 90/08512 A1 | 8/1990 |
| WO | WO 91/04713 A1 | 4/1991 |
| WO | WO 94/10935 A1 | 5/1994 |
| WO | WO 98/32394 | 7/1998 |
| WO | WO 98/44865 A1 | 10/1998 |
| WO | WO 98/58596 A1 | 12/1998 |

OTHER PUBLICATIONS

Ma, Chil-Cheang and Mei-juan Chen. "Vertex-Based Shape Coding in Polar Coordinates for MPEG-4." Taiwan Area Network Conference 1998. Nov. 9-11, 1998. http://tanet98.ndhu.edu.tw/TANET98/HOMEPAGE/paper/2b_1/2b_1.htm.*

Ma, Chil-Cheang et al. "Efficient Shape Coding Algorithm for Object-Oriented Video in MPEG-4." Int'l Conf. on Consumer Electronics (ICCE '99). Jun. 22-24, 1999. pp. 174-175.*

Ba, D.E. et al. "Nonlinear Transform Coding: Polar Coordinates Revisited." Proc. Data Compression Conf. (DCC 2006). Mar. 28-30, 2006.*

Microsoft Press Computer User's Dictionary, © 1998, p. 76-77, and 214-215.*

Watt et al., Advanced Animation and Rendering Techniques, © 1992, pp. 101-110.*

Bohm et al., A survey of curve and surface methods in CAGD, *Computer Aided Geometric Design* (1984) 1:1-60.

Chiappone., Constructing the Gnathologic Setup and Positioner, *JPO, Inc.*, (1980) vol. XIV. No. 2, pp. 121-133.

Cottingham, Gnathologic clear plastic positioner, *American Journal of Orthodontics*, (1969) 55(1):23-31.

Cureton, Correcting Malaligned Mandibular Incisors with Removable Retainers, *JCO Inc.*, (1996) pp. 390-395.

Doyle, Doctors use CAD/CAM to take the pain out of extensive dental procedures, *Computer Graphics World*. (2000) 5 pages total.

Foley et al., Fundamentals of Interactive Computer Graphics, Addison-Wesley Systems Programming Series, (1942) pp. 514-533.

Kesling, The Philosophy of the Tooth Positioning Appliance, *American Journal of Orthodontics and Oral Surgery*, (1945) 31(6):297-304.

Kleeman et al., The Speed Positioner. *JCO, Inc.*, (1996) vol. XXX No. 12, pp. 673-680.

Kuroda et al., Three-dimensional dental cast analyzing system using laser scanning, *American Association of Orthodontists*, (1996) pp. 365-369.

Raintree Essix. <http://www.essix.com/magazine/defaults.html> downloaded from internet Aug. 13, 1997 Essix™ Appliances, 7 pages total.

Redmond et al., Clinical implications of digital orthodontics, *American Association of Orthodontists and Dentofacial Orthopedics*, (2000) 117(2):240-241.

Rogers et al., Mathematical elements for computer graphics, McGraw-Hill Publishing Company (1976) pp. 379-451.

Shilliday Minimizing finishing problems with the mini-positioner, *American Journal of Orthodontics*, (1971) 59:596-599.

Warunek et al., Clinical Use of Silicone Elastomer Appliances, *JCO, Inc.*,(1989) pp. 694-700.

Watt et al., Advanced Animation and Rendering Techniques, ACM Press, (1992) pp. 101-110.

Wells, Application of the positioner appliance in orthodontic treatment, *American Journal of Orthodontics*, (1970) pp. 351-366.

Crocks, CAD/CAM Comes to USC, *USC Dentistry*, (Spring 1990) pp. 14-17.

Curry et al., Integrated Three-Dimensional Craniofacial Mapping at the Craniofacial Research Instrumentation Laboratory/University of the Pacific, *Seminars in Orthodontics*, vol. 7, No. 4 (Dec. 2001), pp. 258-265.

Cutting et al., Three-Dimensional Computer-Assisted Design of Craniofacial Surgical Procedures: Optimization and Interaction with Cephalometric and CT-Based Models, *Plastic and Reconstructive Surgery*, vol. 77. No. 6 (Jun. 1986). pp. 877-885.

DCS Dental AG, The CAD/CAM 'DCS Titan System' for Production of Crowns/Bridges, DSC Production AG, Jan. 1992, pp. 1-7.

Definition for "Gingiva" retrived from the Internet: <<http://reference.com/search/search?q=gingiva>>.

DeFranco et al., Three-Dimensional Large Displacement Analysis of Orthodontic Appliances, *J. Biomechanics*, vol. 9 (1976), pp. 793-801.
Dental Institute University of Zurich Switzerland, Program for International Symposium on Computer Restorations: State of the Art of the CEREC-Method, May 1991, 2 pages total.
Dentrac Corporation, Dentrac document, pp. 4-13.
Doyle, Digital Dentistry, *Computer Graphics World*, Oct. 2000 pp. 50-52, 54.
Duret et al, CAD-CAM in Dentistry, *Journal of the American Dental Association*, vol. 117 (Nov. 1988), pp. 715-720.
Duret et al., CAD/CAM Imaging in Dentistry, *Current Opinion in Dentistry*, vol. 1 (1991), pp. 150-154.
Duret, The Dental CAD/CAM, General Description of the Project, *Hennson International Product Brochure*, Jan. 1986., 18 pages total.
Duret, Vers Une Prostheses Informatisee, (English translation also attached), *Tonus*, vol. 75, (Nov. 15. 1985), pp. 55-57.
Economides, The Microcomputer in the Orthodontic Office, *JCO*, (Nov. 1979), pp. 767-772.
Elasser, Some Observations on the History and Uses of the Kesling Positioner, *Am. J. Orthod.* (1950) 36:368-374.
Faber et al., Computerized interactive orthodontic treatment planning, Am. J. Orthod., vol. 73, No. 1 (Jan. 1978), pp. 3646.
Felton et al. A Computerized Analysis of the Shape and Stability of Mandibular Arch Form, Am. *Journal of Orthodontics and Dentofacial Orthopedics*, vol. 92, No. 6 (Dec. 1987), pp. 478-483.
Friede et al., Accuracy of Cephalometric Prediction in Orthognathic Surgery, Abstract of Papers, *Journal of Dental Research*, vol. 70 (1987), pp. 754-760.
Fütterling et al., "Automated Finite Element Modeling of a Human Mandible with Dental Implants," *WSCG '98 -Conference Program*, retrieved from the Internet: <<http://wscg.zcu.cz/wscg98/papers98/Strasser_98.pdf.>>, 8 pages total.
Gim-Alldent Deutschland, Das DUX System: Die Technik 2 pages total.
Grayson, New Methods for Three Dimensional Analysis of Craniofacial Deformity, Symposium: Computerized Facial Imaging in Oral and Maxiiofacial Surgery, *AAOMS* Sep. 13, 1990,3 pages total.
Guess et al., Computer Treatment Estimates In Orthodontics and Orthognathic Surgery, *JCO*, (Apr. 1989), pp. 262-282.
Heaven et al., Computer-based Image Analysis of Artificial Root Surface Caries, Abstract of Papers, *Journal of Dental Research*, vol. 70,Apr. 17-21, 1991, p. 528.
Hoffmann et al,, Role of Cephalometry for Planning of Jaw Orthopedics and Jaw Surgery Procedures, (Article Summary In English, article in German), *Informatbnen*, (Mar. 1991), pp. 375-396.
Hojjatie et al., "Three-Dimensional Finite Element Analysis of Glass-Ceramic Dental Crowns," *J Biomech.* (1990) vol. 23, No. 11, pp. 1157-1166.
Huckins, CAD-CAM Generated Mandibular Model Prototype from MRI Data, *AAOMS* 1999, p. 96.
JCO Interviews, Craig Andreiko , DDS, MS on the Elan and Orthos Systems, *JCO*, (Aug. 1994), pp. 459-168.
JCO Interviews, Dr. Homer W. Phillips on Computers in Orthodontic Practice, Part 2, *JCO*, (Dec. 1983), pp. 819-831.
Jerrold, The Problem, Electronic Data Transmission and the Law, *AJO-DO*, (Apr. 1988), pp. 478-479.
Jones et al., An Assessment of the Fit of a Parabolic Curve to Pre- and Post-Treatment Dental Arches, *British Journal of Orthodontics*, vol. 16 (1989), pp. 85-93.
Kamada et.al., Case Reports On Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case Reports, J. Nihon University School of Dentistry (1982) 24(1):1-27.
Procera Research Projects, PROCERA Research Projects 1993—Abstract Collection, 1993, pp. 3-28.
Rekow et al., "CAD/CAM for Dental Restorations—Some of the Curious Challenges," *IEEE Transactions on Biomedical Engineering*, (Apr. 1991) vol. 38, No. 4, pp. 344-345.

Rekow et al., "Comparison of Three Data Acquisition Techniques for 3-D Tooth Surface Mapping," *Annual International Conference of the IEEE Engineering in Medicine and Biology Society*, (1991) vol. 13, No. 1, pp. 344-345.
Rekow, A Review of the Developments in Dental CAD/CAM Systems, (contains references to Japanese efforts and content of the papers of particular interest to the clinician are indicated with a one-line summary of their content in the bibliograpy), *Curr Opin Dent*. (Jun. 1992) vol. 2, pp. 25-33.
Rekow, CAD/CAM in Dentisry: A Historical Perspective and View of the Future. *J Can Dent Assoc*, vol. 58 No. 4, (Apr.1992), pp. 283, 287-288.
Rekow, Computer-Aided Design and Manufacturing In Dentisry: A Review of the State of the Art, *The Journal of Prosthetic Dentistry*, vol. 58, No. 4 (Oct. 1987), pp. 512-516.
Rekow, Dental CAD-CAM Systems: What is the State of the Art? *Journal of the American Dental Assoc*, vol. 122 (1991), pp. 43-48.
Rekow, Feasibility of an Automated System for Production of Dental Restorations, PhD Thesis, Univ. of Minnesota, Nov. 1988,244 pages total.
Richmond et.al., The Development of the PAR Index (Peer Assessment Rating): Reliability and Validity, *European Journal of Orthodontics* (1992) 14:125-139.
Richmond, Recording The Dental Cast In Three Dimensions, *Am. J. Orthod. Dentofac. Orthop.*, vol. 92, No. 3, (Sep. 1987), pp. 199-206.
Rudge, Dental arch analysis: arch form, A review of the literature, *European Journal of Orthodontics*, vol. 3, No. 4 (1981), pp. 279-284.
Sakuda et al., Integrated Information-Processing System in Clinical Orthodontics: An Approach with Use of a Computer Network System, *Am. J. Orthod. Dentofac. Orthop*. vol. 101 No. 3 (Mar. 1992), pd. 210-220.
Schellhas et al., Three-Dimensional Computed Tomography in Maxillofacial Surgical Planning, *Arch Otolamgol Head Neck Surg.* vol. 114 (Apr. 1988), pp. 438-442.
Siemens, CEREC—Computer-Reconstruction, High Tech in der Zahnmedizin, 14 page total.
Sinclair, "The Readers' Corner," *Journal of Clinical Orthodontics*, vol. 26, No. 6, (Jun. 1992) pp. 369-372.
Defranco et al., "Three-Dimensional Large Displacement Analysis of Orthodontic Appliances," *J. Biomechanics*, vol. 9 (1976), pp. 793-801.
Dental Institute University of Zurich Switzerland, Program for International Symposium on Computer Restorations: State of the Art of the CEREC-Method, May 1991, 3 pages total.
Duret et al., "CAD-CAM in Dentistry," *Journal of the American Dental Association*, vol. 117 (Nov. 1988), pp. 715-720.
Duret et al., "CAD/CAM imaging in dentistry," *Current Opinion in Dentistry*, vol. 1 (1991), pp. 150-154.
Duret, "The Dental CAD/CAM, General Description of the Project," *Hennson International Product Brochure*, Jan. 1986., 18 pages total.
Duret, "Vers une prosthese informatisee," (English translation also attached), *Tonus*, vol. 75, (Nov. 15, 1985), pp. 55-57.
Economides, "The Microcomputer in the Orthodontic Office," *JCO*, (Nov. 1979), pp. 767-772.
Elasser, "Some observations on the history and uses of the Kesling positioner" *Am. J. Orthod.*, 36:368-374, 1950.
Faber et al., "Computerized interactive orthodontic treatment planning," *Am. J. Orthod.*, vol. 73, No. 1 (Jan. 1978), pp. 36-46.
Felton et al. "A computerized analysis of the shape and stability of mandibular arch form," *Am. Journal of Orthodontics and Dentofacial Orthopedics*, vol. 92, No. 6 (Dec. 1987), pp. 478-483.
Friede et al., "Accuracy of Cephalometric Prediction in Orthognathic Surgery," Abstract of Papers, *Journal of Dental Research*, vol. 70 (1987), pp. 754-760.
Gim-Alldent Deutschland, "Das DUX System: Die Technik" 4 pages total.
Grayson, "New Methods for Three Dimensional Analysis of Craniofacial Deformity," Symposium: Computerized Facial Imaging in Oral and Maxilofacial Surgery, AAOMS Sep. 13, 1990, 3 pages total.
Guess et al., "Computer Treatment Estimates in Orthodontics and Orthognathic Surgery," *JCO*, (Apr. 1989), pp. 262-228.

Heaven et al., "Computer-based Image Analysis of Artificial Root Surface Caries," "Automated Identificaiton of Landmarks in Cephalometric Radiographs," Abstracts of Papers, *Journal of Dental Research*, vol. 67, Mar. 9-13, 1988, 2 pages total.
Rekow, Feasibility of an Automated System for Production of "Dental Restorations," PhD Thesis, Univ. of Minnesota, Nov. 1988, 244 pages total.
Richmond et al., Research Reports, "The development of a 3D Cast Analysis System," *British Journal of Orthodontics*, pp. 53-54.
Richmond, "Recording the dental cast in three dimensions," *Am. J. Orthod. Dentofac. Orthop.*, vol. 92, No. 3, (Sep. 1987), pp. 199-206.
Rudge, "Dental arch analysis: arch form, A review of the literature," *European Journal of Orthodontics*, vol. 3, No. 4 (1981), pp. 279-284.
Sakuda et al., "Integrated information-processing system in clinical orthodontics: An approach with use of a computer network system," *Am. J. Orthod. Dentofac. Ortho.*, vol. 101 No. 3 (Mar. 1992), pp. 210-220.
Schellhas et al., "Three-Dimensional Computer Tomography in Maxillofacial Surgical Planning," *Arch Otolamgol Head Neck Surg.* vol. 114 (Apr. 1988), pp. 438-442.
Segu et al., "Computer-aided Cefalometry and New Mechanics in Orthodontics" (Article Summary in English, article in German), *Fortschr. Kieferorthop.* 44, 370-376 (Nr: 5), 1983.
Shilliday, "Minimizing finishing problems with the mini-positioner" *Am. J. Orthod.* 59:596-599, 1971.
Siemens, "CEREC—Computer-Reconstruction,"High Tech in der Zahnmedizin, 14 page total.
Sirona Dental Systems GmbH, CEREC 3D, Manuel utilisateur, Version 2.0X (in French), 2003, 114 pages total.
Stoll et al., "Computer-aided Technologies in Dentistry" (Article Summary in English, article in German), *Dtsch Zahnärztl Z* 45, 314-322, 1990.
U.S. Department of Commerce, National Technical Information Service, "Automated Crown Replication Using Solid Photography SM," Solid Photography Inc. Melville NY, Oct. 1977, 21 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden et al., Three-Dimensional Analysis of Dental Casts by Means of the Optocom, *J Dent Res*, Jul.-Aug. 1972, p. 1101.
Van Der Linden, "A New Method to Determine Tooth Positions and Dental Arch Dimensions," Jul.-Aug. 1972, p. 1104.
Carnaghan, "An Alternative to Holograms for the Portrayal of Human Teeth" 4th Int Conf. on Holographic Systems, Components and Applications. Sep. 15, 1993. pp. 228-231.
Gao et al. "3-D element Generation for Multi-Connected Complex Dental and Mandibular Structure." Proc. Int'l Workshop on Medical Imaging and Augmented Reality. Jun. 12, 2001, pp. 267-271.
Paul et al. "Digital Documentation of individual Human Jaw and Tooth Forms for Applications in Orthodontics, Oral Surgery and Forensic Medicine" Proc. Of the 24th Annual Conf. of the IEEE Industial Electronics Society (IECON '98). Sep. 4, 1998, pp. 2415-2418.
Verstreken et al. "An Image-Guided Planning System for Endosseous Oral Implants," IEEE Transactions on Medical Imaging. Oct. 1998. vol. 17, Issue 5. pp. 842-852.
Xia et al. "Three-Dimensional Virtual-Reality Surgical Planning and Soft-Tissue Prediction for Orthognathic Surgery." IEEE Transactions on Information Technology in Biomedicine, Jun. 2001. vol. 5, Issue 2, pp. 97-107.
Yamany et al. "A System for Human Jaw Modeling Using Intra-Oral Images", Proc. of the 20th Annual Conf. of the IEE Eng'g in Medicine and Biology Society. Nov. 1, 1998. vol. 2, pp. 563-566.
Cyberware M15 3D Scanner. © 1998-2006. <http://www.headus.com/au/cyberware/m15.html>.
Stawser, D. and Cellini, J., "Training Manual of Ball State University Cyberware Model 15, 3-D Laser Scanner," Dec. 16, 1999 <http://www.bsu.edu/classes/flowers2/training/m15/m15man.html>.
Alcaniz, et al., "An Advanced System for the Simulation and Planning of Orthodontic Treatments," Karl Heinz Hohne and Ron Kikinis (eds.), *Visualization in Biomedical Computing, 4th Int'l. Conf., VBC '96*, Hamburg, Germany, Sep. 22-25, 1996, Springer-Verlag, pp. 511-520.
"The Choice Is Clear: Red, White & Blue . . . The Simple, Affordable, No-Braces Treatment," Allesee Orthodontic Appliances-Pro Lab product information for doctors, <http://ormco.com/aoa/appliancesservices/RWB/doctor.html>, 5 pages (May 19, 2003).
"The Choice is Clear: Red, White & Blue . . . The Simple, Affordable, No-Braces Treatment," Allesee Orthodontic Appliances-Pro Lab product information for patients, <http://ormco.com/aoa/appliancesservices/RWB/patients.html>, 2 pages (May 19, 2003).
"The Choice Is Clear: Red, White & Blue . . . The Simple, Affordable, No-Braces Treatment," Allesee Orthodontic Appliances-Pro Lab product information, 6 pages (2003).
Bartels, et al., *An Introduction to Splines for Use in Computer Graphics and Geometric Modeling*, Morgan Kaufmann Publishers, pp. 422-425 (1987).
Blu, et al., "Linear interpolation revitalized", *IEEE Trans. Image Proc.*, 13(5):710-719 (May 2004).
Boyd et al., "Three Dimensional Diagnosis and Orthodontic Treatment of Complex Malocclusions With the Invisalign Appliance," *Semin. Orthod.*, 7(4):274-293 (Dec 2001).
Burstone (interview), "Dr. Charles J. Burstone on the Uses of the Computer in Orthodontic Practice (Part 1)," *J. Clin. Orthod.*, 13(7):442-453 (Jul. 1979).
Cardinal Industrial Finishes, Powder Coatings information posted at <http://www.cardinalpaint.com> on Aug. 25, 2000, 2 pages.
DENT-X posted on Sep. 24, 1998 at <http://www.dent-x.com/DentSim.htm>, 6 pages.
English translation of Japanese Laid-Open Publication No. 63-11148 to inventory T. Ozukuri (Laid-Open on Jan. 18, 1998) pp. 1-7.
Gottleid et al., "JCO Interviews Dr. James A. McNamura, Jr., on the Frankel Appliance: Part 2: Clinical Management," *J. Clin. Orthod.*, 16(6):390-407 (Jun. 1982).
Highbeam Research, "Simulating Stress Put on Jaw," Tooling & Production [online], Nov. 1996, pp. 1-2, retrieved from the Internet on Nov. 5, 2004, URL <http://static.highbeam.com/t/toolingampproduction/november011996/simulatingstressputonja...>.
Hikage, "Integrated Orthodontic Management System for Virtual Three-Dimensional Computer Graphic Simulation and Optical Video Image Database for Diagnosis and Treatment Planning"*Journal of Japan Orthodontic Society*, Feb. 1987, English translation, pp. 1-38, Japanese version 46(2), pp. 248-269 (60 pages total).
Kochanek, "Interpolating Splines with Local Tension, Continuity and Bias Control," *Computer Graphics*, 18(3):33-41 (Jul. 1984).
Kunii et al., "Articulation Simulation for an Intelligent Dental Care System," *Displays* 15:181-188 (1994).
Manetti, et al., "Computer-Aided Cefalometry and New Mechanics in Orthodontics," (Article Summary in English, article in German). *Fortschr. Kieferothop.* 44, 370-376 (Nr. 5), 1983.
McCann, "Inside the ADA," *J. Amer. Dent. Assoc.*, 118:286-294 (Mar. 1989).
Proffit et al., *Contemporary Orthodontics*, (Second Ed.), Chapter 15, Mosby Inc., pp. 470-533 (Oct. 1993).
Raintree Essix & ARS Materials, Inc., Raintree Essix, Technical Magazine Table of contents and Essix Appliances, <httpz;// www.essix.com/magazine/default.html> Aug. 13, 1997, 7 pages.
Richmond et al., "The Development of the PAR Index (Peer Assessment Rating): Reliability and Validity," *Eur. J. Orthod.*, 14:125-139 (1992).
Schroeder et al., Eds. *The Visual Toolkit*, Prentice Hall PTR, New Jersey (1998) Chapters 6, 8 & 9, (pp. 153-210,309-354, and 355-428, respectively).
Sinclair, "The Readers' Corner," *J. Clin. Orthod.*, 26(6):369-372 (Jun. 1992).
Sturman, "Interative Keyframe Animation of 3-D Articulated Models," Proceedings Graphics Interface '84, May-Jun. 1984, pp. 35-40.
Traux L., "Truax Clasp-Less(TM) Appliance System," *Funct. Orthod.*, 9(5):22-4, 26-8 (Sep.-Oct. 1992).
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL <htp://wscg.zcu.cz/wscg98/wscg98.h>.

Yoshii, "Research on a New Orthodontic Appliance: The Dynamic Positioner (D.P.); I. The D.P. Concept and Implementation of Transparent Silicone Resin (Orthocon)," *Nippon Dental Review*, 452:61-74 (Jun. 1980).

Yoshii, "Research on a New Orthodontic Appliance: The Dynamic Positioner (D.P.); II. The D.P. Manufacturing Procedure and Clinical Applications," *Nippon Dental Review*, 454:107-130 (Aug. 1980).

Yoshii, "Research on a New Orthodontic Appliance: The Dynamic Positioner (D.P.); III.- The General Concept of the D.P. Method and Its Therapeutic Effect, Part 2. Skeletal Reversed Occlusion Case Reports," *Nippon Dental Review*, 458:112-129 (Dec. 1980).

Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," *Nippon Dental Review*, 457:146-164 (Nov. 1980).

Alexander et al., "The DigiGraph Work Station Part 2, Clinical Management," *JCO* (Jul. 1990), pp. 402-407.

Altschuler et al., "Laser Elecro-Optic System for Rapid Three-Dimensional (3D) Topographic Mapping of Surfaces," *OpticalEngineering*, vol. 20(6) (1981), pp. 953-961.

Altschuler et al, "Measuring Surfaces Space-Coded by a Laser- Projected Dot Matrix," *SPIE Imaging Applications for Automated Industrial Inspection and Assembly*, vol. 182 (1979), p. 187-191.

Altschuler et al., "Analysis of 3-D Data for Comparative 3-D Serial Growth Pattern Studies of Oral-Facial Structures," Program and Abstracts of Papers, Feb. 1975, *Journal of Dental Research*, vol. 54, IADR Abstracts 1979, 2 pages total.

Altschuler, "3D Mapping of Maxillo-Facial Prosthesis," AADR Abstract #607,1980, 2 pages total.

American Association for Dental Research, Summary of Activities, Mar. 20-23, 1980, Los Angeles, CA, p. 195.

Andersson et al., "Clinical Results with Titanium Crowns Fabricated with Machine Duplication and Spark Erosion," *Acta Odontological Scandinavia*, vol. 47 (1989), pp. 279-286.

Baumrind et al., "A stereophotogrammetric system for the detection of prosthesis loosening in total hip arthroplasty, Applications of Human Biostereometrics (NATO)," Proceedings of the Society of Photo-Optical Instrumentation Engineers, vol. 166, Jul. 9-13, 1978, pp. 112-123.

Baumrind et al., Mapping the Skull in 3-D, Reprinted from the Journal, *California Dental Association*, vol. 48, No. 2 (1972 Fall Issue) 11 pages total.

Baumrind et al., "Seminars in Orthodontics," *Seminars in Orthodontics*, vol. 7, No. 4 (Dec. 2001), p. 222.

Baumrind, "A System for Craniofacial Mapping Through the Integration of Data from Stereo X-Ray Films and Stereo Photographs," An invited paper submitted to the 1975 American Society of Photogram. Symposium on Close-Range Photogram. Systems, University of Ill. , Aug. 26-30, 1975. pp. 1-25.

Baumrind, "Integrated Three-Dimensional Craniofacial Mapping: Background, Principles, and Perspectives," *Seminars in Orthodontics*. vol. 7, No. 4 (Dec. 2001), pp. 223-232.

Begole et al., "A Computer System for the Analysis of Dental Casts," *The Angle Orthodontist*, vol. 51 No. 3 (Jul. 1981), pp. 253-259.

Bernard et al., "Computerized diagnosis in Orthodontics for Epidemiological Studies" (progress report), Abstracts of Papers, *Journal of Dental Research*; vol. 71, Special Issue Mar. 1-14, 1992, pp. 28-36.

Bhatia et al., "A Computer-Aided Design for Orthognathic Surgery," *British Journal of Oral and Maxillofacial Surgery*, vol. 22 (1984), pp. 237-253.

Biggerstaff et al., "Computerized analysis of occlusion in the postcanine dentition," *American Journal of Orthodontics*, vol. 61, No. 3 (Mar. 1972), pp. 244-254.

Biggerstaff, "Computerized Diagnostic Setups and Simulations," *The Angle Orthodontist*, vol. 40, No. 1 (Jan. 1970), pp. 28-36.

Brandestini et al., "Computer Machined Ceramic Inlays: In Vitro Marginal Adaptation," *Journal of Dental Research*, vol. 64/Special Issue/Abstracts, IADR/AADR Abstracts 1985, 1 page total.

Brook et al., An Image Analysis System for the Determination of Tooth Dimensions from Study Casts: Comparision with Manual Measurements of Mesio-distal Diameter, Abstract of Papers, 1985, Dept. of Children's Dentistry and Orthodontics, *J Dent Res.*, Mar. 1986, pp. 428-431.

Burstone (interview), "Dr. Charles J. Burstone on The Uses of the Computer in Orthodontic Practice (Parts 1 and 2)," *Journal of Clinical Orthodontics*, (Part 1) vol. 8, No. 7 , Jul. 1979; (Part 2) vol. 8, No. 8 pp. 539-551, Aug. 1979.

Burstone et al., "Precision adjustment of the transpalatal lingual arch: Computer arch form predetermination," *Am. Journal of Orthodontics*, vol. 79, No. 2 (Feb. 1981), pp. 115-133.

Chaconas et al., "The DigiGraph Work Station, Part 1, Basic Concepts," *JCO* (Jun. 1990), pp. 360-367.

Chafetz et al., "Subsidence of the Femoral Prosthesis, A Stereophotogrammetric Evaluation," *Clinical Orthopaedics and Related Research*, No. 201 (Dec. 1985), pp. 60-67.

Chiappone, "Constructing the gnathologic setup and positioner" *J. Clin. Orthod.*, 14:121-133, 1980.

Cottingham, "Gnathologic clear plastic positioner" *Am. J. Orthod.*, 55:23-31, 1969.

Crawford, "Computers in Dentistry: Part 1: CAD/CAM: The Computer Moves Chairside," "Part 2: F. Duret—A Man With A Vision," "Part 3: The Computer Gives New Vision- Literally," "Part 4: Bytes 'N Bites" The Computer Moves From The Front Desk To The Operatory, *Canadian Dental Journal*, vol. 54(9), , (1988), pp. 661-666.

Crawford, "CAD/CAM in the Dental Office: Does It Work?" *Canadian Dental Journal*, vol. 57, No. 2 (Feb. 1991), pp. 121-123.

Crooks, "CAD/CAM Comes to USC," *USC Dentistry*, (Spring 1990) pp. 14-17.

Cureton, "Correcting malaligned mandibular incisors with removable retainers" *J. Clin. Orthod.*, 30:390-395, 1996.

Curry et al., "Integrated Three-Dimensional Craniofacial Mapping at the Craniofacial Research Instrumentation Laboratory/University of the Pacific," *Seminars in Orthodontics*, vol. 7, No. 4 (Dec. 2001), pp. 258-265.

Cutting et al., "Three-Dimensional Computer-Assisted Design of Craniofacial Surgical Procedures: Optimization and Interaction with Cephalometric and CT-Based Models," *Plastic and Reconstructive Surgery*, vol. 77, No. 6 (Jun. 1986), pp. 877-885.

DCS Dental AG, "The CAD/CAM 'DCS Titan System' for Production of Crowns/Bridges" *DSC Production AG*, Jan. 1991, pp. 1-7.

Hoffmann et al., "Role of Cephalometry for Planning of Jaw Orthopedics and Jaw Surgery Procedures," (Article Summary in English, article in German), *Informationen*, (Mar. 1991), pp. 375-396.

Huckins, "CAD-CAM Generated Mandibular Model Prototype from MRI Data," *AAOMS* 1999, p. 96.

Inside the ADA, *Journal Of The American Dental Assoc.*, vol. 118 (Mar. 1989) 9 pages total.

JCO Interviews, "Craig Andreiko , DDS, MS on the Elan and Orthos Systems", JCO, (Aug. 1994), pp. 459-468.

JCO Interviews, "Dr. Homer W. Phillips on Computers in Orthodontic Practice, Part 2," JCO, (Dec. 1983), pp. 819-831.

Jerrold, "The problem, electronic data transmission and the law," *AJO-DO*, (Apr. 1988), pp. 478-479.

Jones et al., "An Assessment of the Fit of a Parabolic Curve to Pre- and Post-Treatment Dental Arches," *British Journal of Orthodontics*, vol. 16 (1989), pp. 85-93.

Kamada et al., "Case reports on tooth positioners using LTV vinyl silicone rubber" J. Nihon University School of Dentistry, 26(1):11-29, 1984.

Kamada et al., "Construction of tooth positioners with LTV vinyl silicone rubber and some case reports" J. Nihon University School of Dentistry, 24(1):1-27, 1982.

Kanazawa et al., "Three-Dimensional Measurements of the Occlusal Surfaces of Upper Molars in a Dutch Population," *J. Dent Res.* , vol. 63, No. 11 (Nov. 1984), pp. 1298-1301.

Kesling, "Coordinating the predetermined pattern and tooth positioner with conventional treatment" *Am. J. Orthod. Oral. Surg.*, 32:285-293, 1946.

Kesling, "The philosophy of the tooth positioning appliance" *Am. J. Orthod. Oral. Surg.*, 31(6):297-304, 1945.

Kleemann et al., "The speed positioner" *J. Clin. Orthod.*, 30:673-680, 1996.

Kuroda et al., "Three-dimensional dental cast analyzing system using laser scanning" *Am. J. Orthod. Dentofac. Orthop.*, 110:365-369, 1996.

Laurendeau et al., "A Computer-Vision Technique for the Acquisition and Processing of 3-D Profiles of Dental Imprints: An Application in Orthodontics," *IEEE Transactions on Medical Imaging*, vol. 10, No. 3 (Sep. 1991), pp. 453-461.

Leinfelder et al., "A new method for generating ceramic restorations: a CAD-CAM system," *Journal Of The American Dental Assoc.*, vol. 118, No. 6 (Jun. 1989), pp. 703-707.

McNamara et al., *Orthodontic and Orthopedic Treatment in the Mixed Dentition*, Needham Press, Jan. 1993. pp. 347-353.

McNamara et al., "Invisible Retainers", *J. Clinical Orthodontics*, (Aug. 1985) pp. 570-578.

Moermann et al., "Computer Machined Adhesive Porcelain Inlays: Margin Adaptation after Fatigue Stress," IADR Abstract 339, *Journal of Dental Research*, vol. 66(a) (1987), p. 339.

Mörmann et al., "Marginal Adaptation von adhasiven Porzellaninlays in vitro,"*Schwizerische Monatsschrift fur Zahnmedizin*, vol. 85 (1985), p. 1118-1129.

Mörmann et al., "Marginal Adaptation von adhäsuven Porzellaninlays in vitro," Separatdruck aus: Schweiz. Mschr. Zahnmed. 95: 1118, 1985.

Nahoum, "The vacuum formed dental contour appliance" *The New York State Dental Journal*, 30(9):385-390, Nov. 1964.

Nash, "CEREC CAD/CAM Inlays: Aesthetics and Durability in a Single Appointment," *Dentistry Today*. (Oct 1990), pp. 20, 22-23, 54.

Nishiyama et al., "A new construction of tooth repositioner by LTV vinyl silicone rubber" J. Nihon University School of Dentistry, 19(2):93-102, 1977.

Pinkham, "'Foolish' Concept Propels Technology," *Dentist*, Jan./Feb. 1989, 3 pages total.

Pinkham, "Inventor's CAD/CAM may transform dentistry," *Dentist*, Sep. 1990, 3 pages total.

Ponitz, Invisible Retainers, 59 *Am. J. Orthodontics*, Mar. 1971, pp. 266-272.

Procera Research Projects, *PROCERA Research Projects 1993*—Abstract Collection, 1993, pp. 3-28.

Rekow, "A Review of the Developments in Dental CAD/CAM Systems,"(contains references to Japanese efforts and content of the papers of particular interest to the clinician are indicated with a one-line summary of their content in the bibliography), Dental Clinics: *Prosthodontics and Endodontics*, pp. 25-33, 1992.

Rekow, "CAD/CAM in Dentistry: A Historical Perspective and View of the Future," *Journal*, vol. 58 No. 4, (Apr. 1992), pp. 283, 287-288.

Rekow, "Computer-Aided Design and Manufacturing in Dentistry: A Review of the State of the Art," *The Journal of Prosthetic Dentistry*, vol. 58, No. 4 (Oct. 1987), pp. 512-516.

Rekow, "Dental CAD-CAM Systems: What is the State of the Art?" *Journal of the American Dental Assoc.*, vol. 122 (1991), pp. 43-48.

Van Der Zel, "Ceramic-fused-to-metal Restorations witnh a New CAD/CAM System," *Quintessence International*, vol. 24(11) (1993), pp. 769-778.

Várady et al., "Reverse Engineering of Geometric Models—An Introduction," May 13, 1996, pp. 1-28.

Warunek et al., "Clinical use of silicone elastomer appliances" *JCO*, MH (10):694-700, 1989.

Warunek et al., "Physical and mechanical properties of elastomers in orthodontic positioners" *Am. J. Orthod. Dentofac. Orthop.*, 95:388-400, 1989.

Wells, "Application of the positioner appliance in orthodontic treatment" *Am. J. Orthodont.*, 58:351-366, 1970.

Williams, "Dentistry and CAD/CAM: Another French Revolution,"*Journal of Dental Practice Admin.*, Jan./Mar. 1987, pp. 2-5.

Williams, "The Switzerland and Minnesota Developments in CAD/CAM," *Journal of Dental Practice Admin.*, pp. 50-55, Apr. /Jun. 1987.

Wishan, "New Advances in Personal Computer Applications for Cephalometric Analysis, Growth Prediction, Surgical Treatment Planning and Imaging Processing,"Symposium: Computerized Facial Imaging in Oral and Maxilofacial Surgery, AAOMS, Sep. 13, 1990, p. 5.

Yamamoto et al., "Three-Dimensional Measurement of Dental Cast Profiles and Its Applications to Orthodontics," Annual Int'l Conf. of IEEE Engineering in Medicine and Biology Society, vol. 12, No 5, pp. 2051-2053, 1990.

Yamamoto et al., "Optical measurement of dental cast profile and application to analysis of three-dimensional tooth movement in orthodontics," *Frontiers in Med. and Biol. Eng'g*, vol. 1, No. 2 (1988), pp. 119-130.

"Simulating Stress on Jaws: Ansys Inc's Finite Element Analysis Software," Tooling & Production, (Nov. 1996).

Alexander et al., The DigiGraph Work Station Part 2, Clinical Management, *JCO* (Jul. 1990), pp. 402-407.

Altschuler et al, Measuring Surfaces Space-Coded by a Laser-Projected Dot Matrix, *SPIE Imaging Applications for Automated Industrial Inspection and Assembly*, vol. 182 (1979), p. 187-191.

Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, *Journal of Dental Research*, vol. 58, Jan. 1979, Special Issue A, p. 221.

Altschuler et al., Laser Electro-Optic System for Rapid Three-Dimensional (3D) Topographic Mapping of Surfaces, *Optical Engineering*, vol. 20, No. 6. (1981), pp. 953-661.

Altschuler, 3D Mapping of Maxillo-Facial Prosthesis, AADR Abstract #607, 1980, 2 pages total.

Andersson et al., Clinical Results with Titanium Crowns Fabricated with Machine Duplication and Spark Erosion, *Acta Odontological Scandinavia*, vol. 47 (1989), pp. 279-286.

Baumrind et al., A Stereophotogrammetric System for the Detection of Prosthesis Loosening in Total Hip Arthroplasty, NATO Symposium on Applications of Human Biostereometrics, Jul. 9-13, 1978, *SPIE* ,vol. 166, pp. 112-123.

Baumrind, "A System for Craniofacial Mapping Through the Integration of Data from Stereo X-Ray Films and Stereo Photographs, " An invited paper submitted to the 1975 American Society of Photogram. Symposium on Close-Range Photogram. Systems, University of Ill., Aug. 26-30, 1975, pp. pp. 142-166.

Baumrind, Integrated Three-Dimensional Craniofacial Mapping: Background, Principles, and Perspectives, *Seminars in Orthodontics*, vol. 7, No. 4 (Dec. 2001), pp. 223-232.

Begole et al., A Computer System for the Analysis of Dental Casts, *The Angle Orthodontist*, vol. 51 No. 3 (Jul. 1981), pp. 253-259.

Bernard et al., Computerized Diagnosis in Orthodontics for Epidemiological Studies: A Progress Report, Paper presented at International Association for Dental Research 66th General Session, Mar. 9-13, 1988, Montreal, Canada. The abstract is published in *J Dental Res Special Issue*, vol. 67, p. 169.

Bhatia et al, A Computer-Aided Design for Orthognathic Surgery. *British Journal of Oral and Maxillofacial Surgery*, vol. 22 (1984), pp. 237-253.

Biggerstaff et al., Computerized Analysis of Occlusion in the Postcanine Dentition, *Amercan Journal of Orthodontics*, vol. 61, No. 3 (Mar. 1972), pp. 245-254.

Biggerstaff, Computerized Diagnostic Setups and Simulations, *The Angle Orthodontist*, vol. 40, No. 1 (Jan. 1970), pp. 28-36.

Bourke, "Coordinate System Transformation," (Jun. 1996) retrieved from the Internet <<http://astronomy.swin.edu.au/~pbourke/projection/coords>>.

Brandestini et al., Computer Machined Ceramic Inlays: In Vitro Marginal Adaptation, *Journal of Dental Research*, vol. 64/Special Issue/Abstracts, IADR/AADR Abstracts 1985, p. 208.

Brook et al., An Image Analysis System for the Determination of Tooth Dimensions from Study Casts: Comparison with Manual Measurements of Mesio-distal Diameter, *J Dent Res.*, vol. 65, No. 3, Mar. 1986, pp. 428-431.

Burstone (interview), Dr. Charles J. Burstone on The Uses of the Computer in Orthodontic Practice (Part 1), *Journal of Clinical Orthodontics*, (Jul. 1979), vol. 13. No. 7, pp. 442-453.

Burstone (interview), Dr. Charles J. Burstone on The Uses of the Computer in Orthodontic Practice (Part 2), *Journal of Clinical Orthodontics*, (Aug. 1979), vol. 13, No. 8, pp. 539-551.

Burstone et al., Precision Adjustment of the Transpalatal Lingual Arch: Computer Arch Form Predetermination, *Am, Journal of Orthodontics*, vol. 79, No. 2 (Feb. 1981), pp. 115-133.

Chanconas et al., The DigiGraph Work Station, Part 1, Basic Concepts, *JCO* (Jun. 1990), pp. 360-367.

Chafetz et al., Subsidence of the Femoral Prosthesis, A Stereophotogrammetric Evaluation, *Clinical Orthopedics and Related Research*, No. 201 (Dec. 1985), pp. 60-67.

Crawford, CAD/CAM in the Dental Office: Does It Work? *Canadian Dental Journal*, vol. 57, No. 2 (Feb. 1991), pp. 121-123.

Kanazawa et al., Three-Dimensional Measurements of the Occlusal Surfaces of Upper Molars in a Dutch Population, *J. Dent Res.*, vol. 63, No. 11 (Nov. 1984), pp. 1298-1301.

Kesling, Coordinating the Predetermined Pattern and Tooth Positioner with Conventional Treatment, *Am. J. Orthod. Oral Surg.* (1946) 32:285-293.

Laurendeau et al, A Computer-Vision Technique for the Acquisition and Processing of 3-D Profiles of Dental Imprints: An Application in Orthodontics, IEEE Transactions on Medical Imaging, vol. 10, No. 3 (Sep. 1991), pp. 453-461.

Leinfelder et al, A New Method for Generating Ceramic Restorations: a CAD-CAM system, *Journal of the American Dental Assoc*, vol. 118, No. 6 (Jun. 1989), pp. 703-707.

Manetti et al., Computer-aided Cefalometry and New Mechanics in Orthodontics (Article Summary in English, article in German), *Fortschr. Kieferorthop.* 44, 370-376 (Nr. 5), 1983.

McCann, Inside the ADA, *Journal Of The American Dental Assoc*, vol. 118 (Mar. 1989) pp. 286-294.

McNamara et al, Invisible Retainers, *J. Clinical Orthodontics*, (Aug. 1985) pp. 570-578.

McNamara et al, *Orthodontic and Orthopedic Treatment in the Mixed Dentition*, Needham Press, Jan. 1993, pp. 347-353.

Moermann et al, Computer Machined Adhesive Porcelain Inlays: Margin Adaptation after Fatigue Stress, IADR Abstract 339, *Journal of Dental Research*, vol. 66(a) (1987), p. 763.

Mörmann et al., "Marginale Adaptation von adhäsuven Porzellaninlays in vitro," Separatdruck aus: Schweiz. Mschr. Zahnmed. 95: 1118-1129, 1985.

Nahoum, "The Vacuum Formed Dental Contour Appliance," *The New York State Dental Journal*, (Nov. 1964) vol. 30, No. 9, pp. 385-390.

Nash, Cerec CAD/CAM Inlays: Aesthetics and Durability in a Single Appointment, *Dentistry Today*, (Oct. 1990), pp. 20, 22-23, 54.

Nishiyama et al., A New Construction of Tooth Repositioner by LTV Vinyl Silicone Rubber, J. Nihon University School of Dentistry (1977) 19(2):93-102.

Pinkham, 'Foolish' Concept Propels Technology, *Dentist*, Jan./Feb. 1989, 3 pages total.

Pinkham, Inventor's CAD/CAM May Transform Dentistry, *Dentist*, Sep. 1990, 3 pages total.

Ponitz, Invisible Retainers, *Am J. Orthod,*. vol. 59, No. 3 (Mar. 1971) pp. 266-272.

Sirona Dental Systems GmbH, *CEREC 3D, Manuel utiiisateur*, Version 2.0X (in French), 2003, 114 pages total.

Stoll et al., Computer-aided Technologies in Dentistry (Article Summary in English, article in German), *Dtsch Zahna'rztl Z* 45, 314-322, 1990.

U.S. Department of Commerce, National Technical Information Service, Automated Crown Replication Using Solid Photography SM, Solid Photography Inc. Melville NY, Oct. 1977, 20 pages total.

U.S. Department of Commerce, National Technical Information Service, Holodontography: An Introduction to Dental Laser Holography, School of Aerospace Medicine Brooks AFB Tex, Mar. 1973, 37 pages total.

U.S. Appl. No. 60/050,342, filed on Jun. 20, 1997, 41 pages total.

Van Der Linden et al., Three-Dimensional Analysis of Dental Casts by Means of the Optocom, *J Dent Res*, Jul.-Aug. 1972, p. 1100.

Van Der Linden, A New Method to Determine Tooth Positions and Dental Arch Dimensions, *J Dent Res*, Jul.-Aug. 1972, vol. 51, No. 4, p. 1104.

Van Der Zel, Ceramic-fused-to-metal Restorations with a New CAD/CAM System, *Quintessence International*, vol. 24, No. 11 (1993), pp. 769-778.

Varady et al., Reverse Engineering Of Geometric Models—An Introduction, *Computer-Aided Design*, 29 (4):255-268, 1997.

Warunek et al., Physial and Mechanical Properties of Elastomers in Orthodonic Positioners, *Am. J. Orthod. Dentofac. Orthop*, vol. 95, No. 5, (May 1989) pp. 399-400.

Williams, Dentistry and CAD/CAM: Another French Revolution, *Journal of Dental Practice Admin.*, Jan./Mar. 1987, pp. 2-5.

Williams, The Switzerland and Minnesota Developments in CAD/CAM, *Journal of Dental Practice Admin.*, pp. 50-55, Apr./Jun. 1987.

Wishan, New Advances in Personal Computer Applications for Cephalometric Analysis, Growth Prediction, Surgical Treatment Planning and Imaging Processing, Symposium: Computerized Facial Imaging in Oral and Maxilofacial Surgery Presented on Sep. 13, 1990.

Yamamoto et al., Optical Measurement of Dental Cast Profile and Application to Analysis of Three-Dimensional Tooth Movement in Orthodontics, *Frontiers in Med. and Biol. Eng'g*, vol. 1, No. 2 (1988), pp. 119-130.

Yamamoto et al., Three-Dimensional Measurement of Dental Cast Profiles and its Applications to Orthodontics, *Annual Int'l Conf. of IEEE Engineering in Medicine and Biology Society*, vol. 12, No. 5 (1990), pp. 2051-2053.

* cited by examiner

EFFICIENT DATA REPRESENTATION OF TEETH MODEL

CROSS-REFERENCES TO RELATED APPLICATIONS

The present application is a continuation of U.S. application Ser. No. 10/359,998, filed on Feb. 7, 2003, which was a continuation of U.S. application Ser. No. 09/576,721, filed May 23, 2000 (now issued as U.S. Pat. No. 6,633,789), which was a continuation-in-part of U.S. application Ser. No. 09/506,419, filed on Feb. 17, 2000 (now issued as U.S. Pat. No. 6,463,344), the full disclosures of which are incorporated herein by reference.

BACKGROUND OF THE INVENTION

1. Field of the Invention

The invention relates generally to the field of orthodontics and, more particularly, to computer modeling of teeth.

2. Description of the Background Art

Tooth positioners for finishing orthodontic treatment are described by Kesling in the *Am. J. Orthod. Oral. Surg.* 31:297-304 (1945) and 32:285-293 (1946). The use of silicone positioners for the comprehensive orthodontic realignment of a patient's teeth is described in Warunek et al. (1989) *J. Clin. Orthod.* 23:694-700. Clear plastic retainers for finishing and maintaining tooth positions are commercially available from Raintree Essix, Inc., New Orleans, La. 70125, and Tru-Tain Plastics, Rochester, Minn. 55902. The manufacture of orthodontic positioners is described in U.S. Pat. Nos. 5,186,623; 5,059,118; 5,055,039; 5,035,613; 4,856,991; 4,798,534; and 4,755,139.

Other publications describing the fabrication and use of dental positioners include Kleemann and Janssen (1996) *J. Clin. Orthodon.* 30:673-680; Cureton (1996) *J. Clin. Orthodon.* 30:390-395; Chiappone (1980) *J. Clin. Orthodon.* 14:121-133; Shilliday (1971) *Am. J. Orthodontics* 59:596-599; Wells (1970) *Am. J. Orthodontics* 58:351-366; and Cottingham (1969) *Am. J. Orthodontics* 55:23-31.

Kuroda et al. (1996) *Am. J. Orthodontics* 110:365-369 describes a method for laser scanning a plaster dental cast to produce a digital image of the cast. See also U.S. Pat. No. 5,605,459.

U.S. Pat. Nos. 5,533,895; 5,474,448; 5,454,717; 5,447,432; 5,431,562; 5,395,238; 5,368,478; and 5,139,419, assigned to Ormco Corporation, describe methods for manipulating digital images of teeth for designing orthodontic appliances.

U.S. Pat. No. 5,011,405 describes a method for digitally imaging a tooth and determining optimum bracket positioning for orthodontic treatment. Laser scanning of a molded tooth to produce a three-dimensional model is described in U.S. Pat. No. 5,338,198. U.S. Pat. No. 5,452,219 describes a method for laser scanning a tooth model and milling a tooth mold. Digital computer manipulation of tooth contours is described in U.S. Pat. Nos. 5,607,305 and 5,587,912. Computerized digital imaging of the jaw is described in U.S. Pat. Nos. 5,342,202 and 5,340,309. Other patents of interest include U.S. Pat. Nos. 5,549,476; 5,382,164; 5,273,429; 4,936,862; 3,860,803; 3,660,900; 5,645,421; 5,055,039; 4,798,534; 4,856,991; 5,035,613; 5,059,118; 5,186,623; and 4,755,139.

BRIEF SUMMARY OF THE INVENTION

A computer-implemented method generates a computer model of one or more teeth by receiving as input a digital data set of meshes representing the teeth; selecting a curved coordinate system with mappings to and from a 3D space; and generating a function in the curved coordinate system to represent each tooth.

Advantages of the system include one or more of the following. The system reduces the amount of data storage space required for storing and communicating teeth treatment information. By utilizing space more efficiently, the system reduces the cost of the system, improves the responsiveness of the system, and allows additional functionality to be implemented.

The system supports fast distance estimation from a point to the tooth's surface. This capability is needed for rapid collision detection. It also supports smoothing of the tooth surface—for noise reduction. Such rapid collision detection may support real-time manipulation of the teeth for treatment. For example, a user moves a tooth, and the tooth stops when it comes in contact with another tooth.

The system can also support patching small holes in the model of the teeth that may be generated during the taking of impressions/negative impressions. The system also provides the user with a selectable range of precision in teeth geometry representation.

The system also allows visualization to be used to communicate treatment information in a computer-automated orthodontic treatment plan and appliance. The invention generates a realistic model of the patient's teeth without requiring a user to possess in-depth knowledge of parameters associated with patient dental data compression. Additionally, expertise in 3D software and knowledge of computer architecture is no longer needed to process and translate the captured medical data into a realistic computer model rendering and animation.

The invention allows teeth plan treatment to be generated and communicated in a simple and efficient manner. It also improves the way a treating clinician performs case presentations by allowing the clinician to express his or her treatment plans more clearly and gives a prospective patients an opportunity to visualize the facial changes associated with the proposed treatment. The invention allows multidisciplinary work teams to deal easily and efficiently with the treatment plan. Another major benefit is the ability to visualize and interact with models and processes without the attendant danger, impracticality, or significantly greater expense that would be encountered in the same environment if it were physical. Thus, money and time are saved while the quality of the treatment plan is enhanced.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

Systems and methods are provided for modeling teeth in creating a treatment plan. The systems and methods compress data associated with the teeth model to reduce the storage size and transmission time to a treating professional. Based on the treatment plan, the teeth can be incrementally moved using a plurality of discrete appliances, where each appliance successively moves one or more of the patient's teeth by relatively small amounts.

Figure 1A:
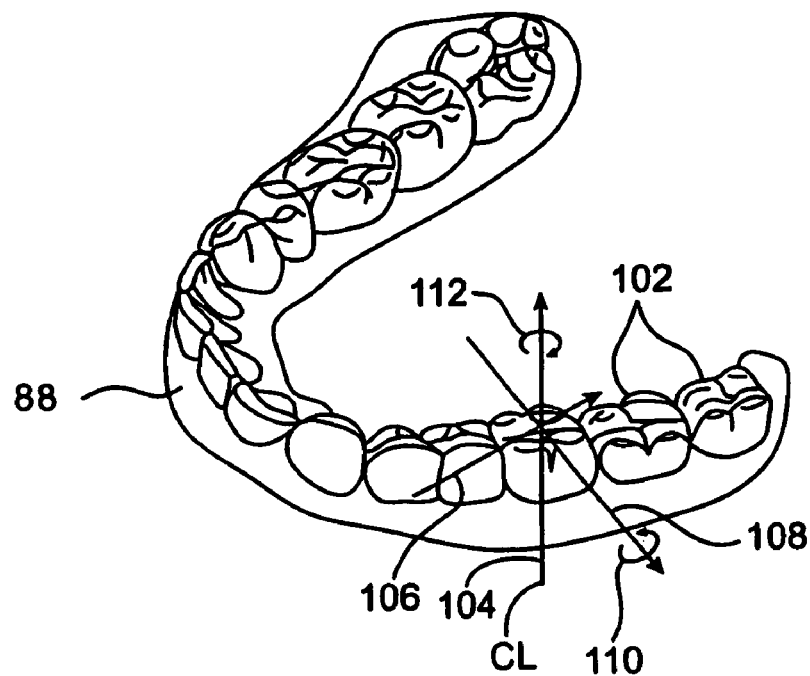
FIG. 1A illustrates a patient's jaw and provides a general indication of how teeth may be moved.

Referring now to FIG. 1A, a representative jaw 88 includes sixteen teeth, at least some of which are to be moved from an initial tooth arrangement to a final tooth arrangement. To understand how the teeth may be moved, an arbitrary centerline (CL) is drawn through one of the teeth 102. With reference to this centerline (CL), the teeth may be moved in the orthogonal directions represented by axes 104, 106, and 108 (where 104 is the centerline). The centerline may be rotated about the axis 108 (root angulation) and 104 (torque) as indicated by arrows 110 and 112, respectively. Additionally, the tooth may be rotated about the centerline. Thus, all possible free-form motions of the tooth can be performed.

Figure 1B:
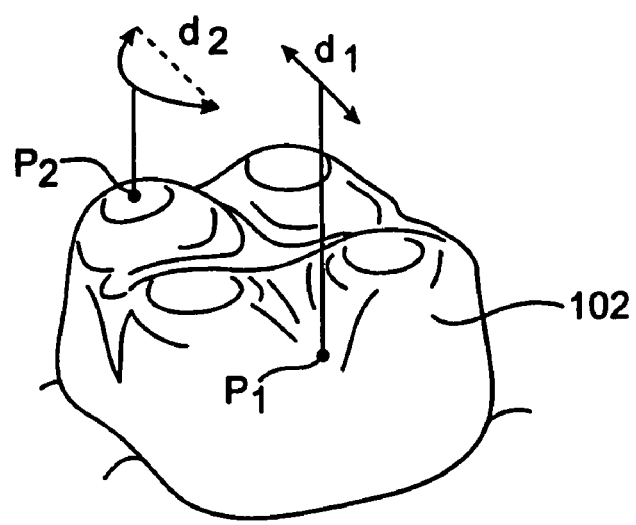
FIG. 1B illustrates a single tooth from FIG. 1A and defines how tooth movement distances are determined.

Referring now to FIG. 1B, the magnitude of any tooth movement is defined in terms of the maximum linear translation of any point P on a tooth 102. Each point $P_i$ will undergo a cumulative translation as that tooth is moved in any of the orthogonal or rotational directions defined in FIG. 1A. That is, while the point will usually follow a non-linear path, there will be a linear distance between any point in the tooth when determined at any two times during the treatment. Thus, an arbitrary point $P_1$ may in fact undergo a true side-to-side translation as indicated by arrow $d_1$, while a second arbitrary point $P_2$ may travel along an arcuate path, resulting in a final translation $d_2$. In many situations, the maximum permissible movement of a point $P_i$ in any particular tooth is defined as the maximum linear translation of that point $P_i$ on the tooth that undergoes the maximum movement for that tooth in any treatment step.

One tool for incrementally repositioning the teeth in a patient's jaw is a set of one or more adjustment appliances. Suitable appliances include any of the known positioners, retainers, or other removable appliances which are used for finishing and maintaining teeth positions in connection with conventional orthodontic treatment. As described below, a plurality of such appliances can be worn by a patient successively to achieve gradual tooth repositioning. A particularly advantageous appliance is the appliance 100, shown in FIG. 1C, which typically comprises a polymeric shell having a cavity shaped to receive and resiliently reposition teeth from one tooth arrangement to another tooth arrangement. The polymeric shell typically fits over all teeth present in the upper or lower jaw. Often, only some of the teeth will be repositioned while others will provide a base or anchor region for holding the repositioning appliance in place as it applies the resilient repositioning force against the tooth or teeth to be repositioned. In complex cases, however, many or most of the teeth will be repositioned at some point during the treatment. In such cases, the teeth which are moved can also serve as a base or anchor region for holding the repositioning appliance. The gums and the palette also serve as an anchor region in some cases, thus allowing all or nearly all of the teeth to be repositioned simultaneously.

Figure 1C:
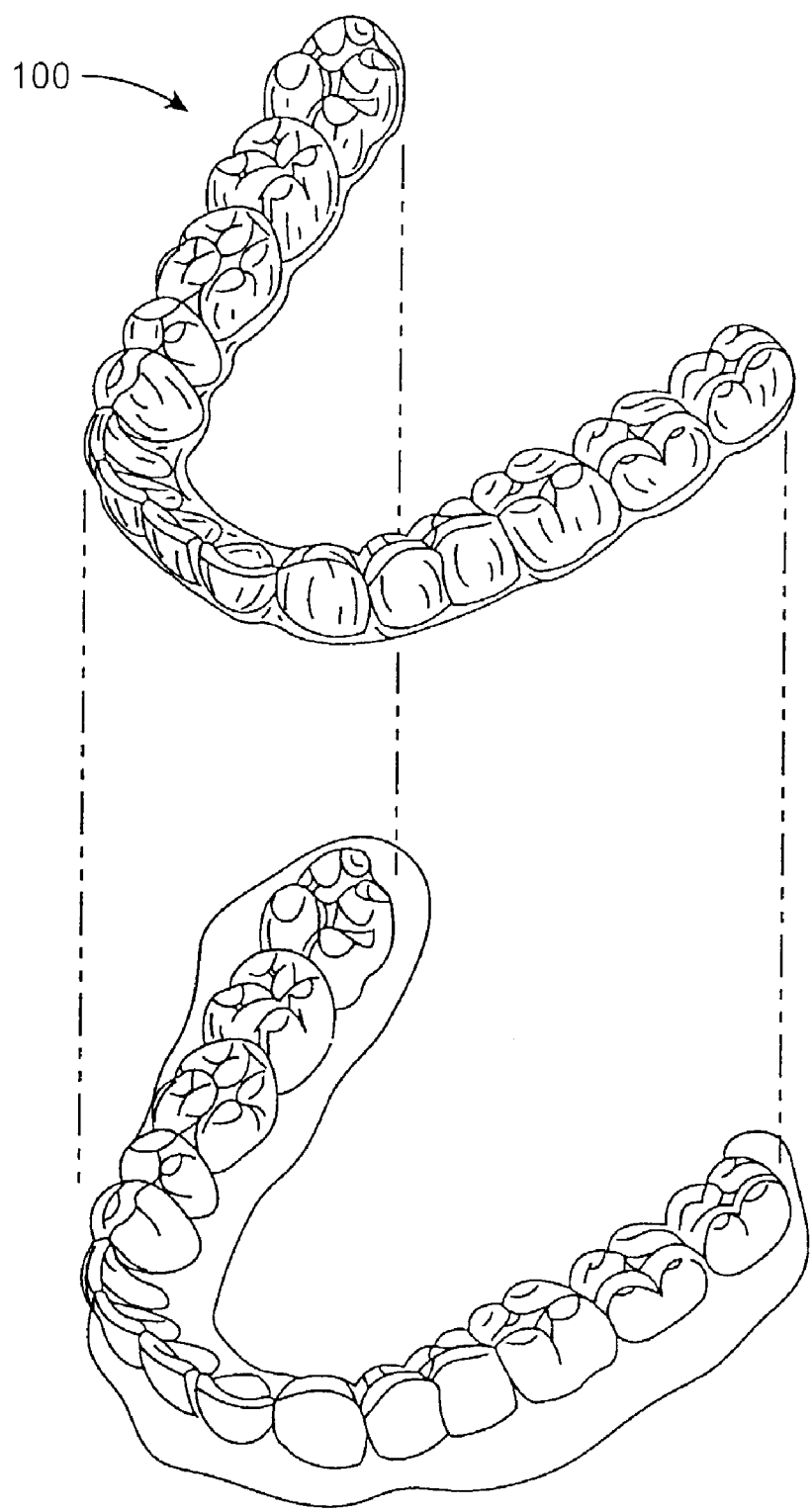
FIG. 1C illustrates the jaw of FIG. 1A together with an incremental position adjustment appliance.

The polymeric appliance 100 of FIG. 1C is preferably formed from a thin sheet of a suitable elastomeric polymeric, such as Tru-Tain 0.03 in thermal forming dental material, marketed by Tru-Tain Plastics, Rochester, Minn. 55902. In many cases, no wires or other means are provided for holding the appliance in place over the teeth. In some cases, however, it is necessary to provide individual attachments on the teeth with corresponding receptacles or apertures in the appliance 100 so that the appliance can apply forces that would not be possible or would be difficult to apply in the absence of such attachments.

Figure 2:
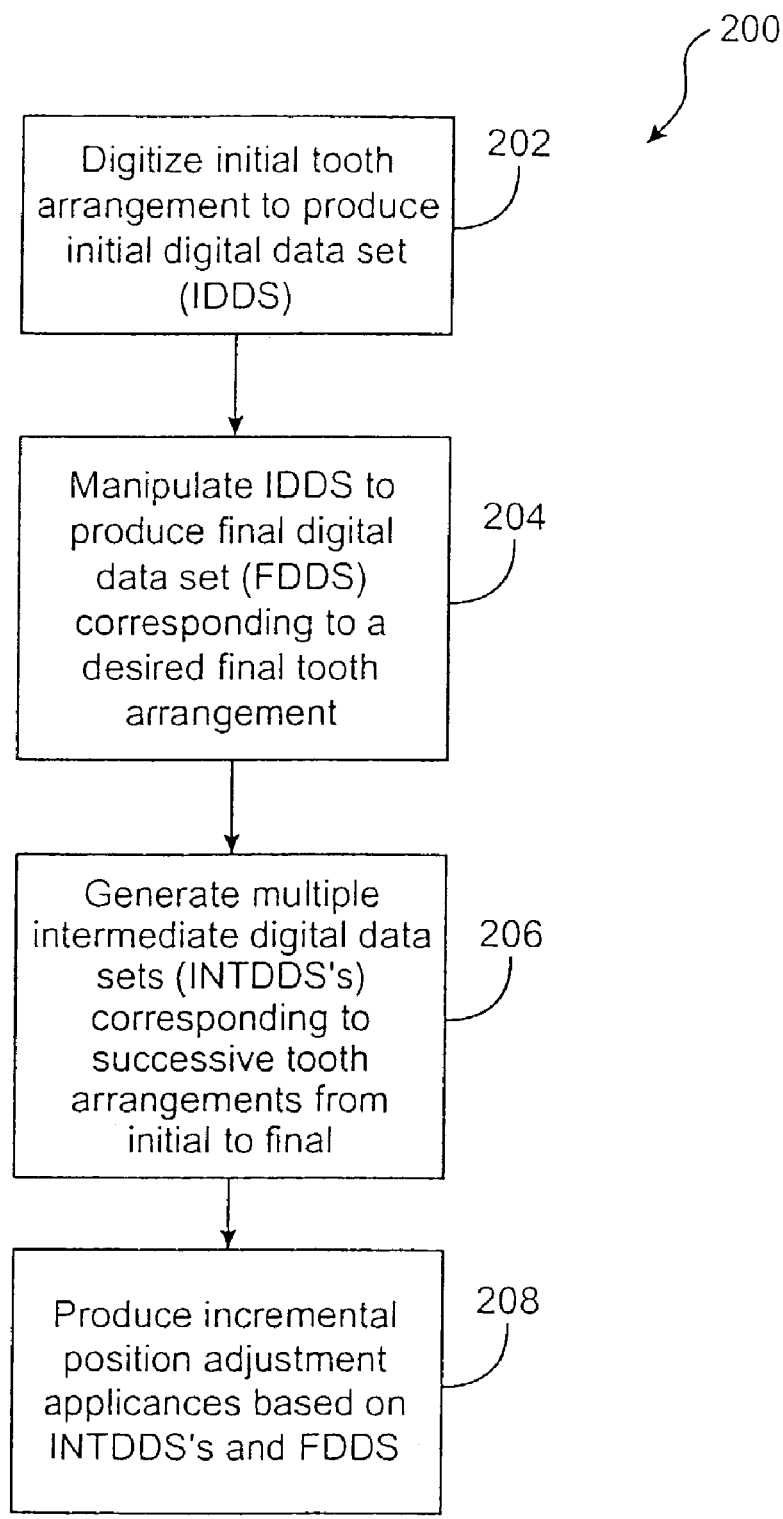
FIG. 2 is a block diagram illustrating steps for producing a system of incremental position adjustment appliances.

FIG. 2 shows a process 200 for producing the incremental position adjustment appliances for subsequent use by a patient to reposition the patient's teeth. As a first step, an initial digital data set (IDDS) representing an initial tooth arrangement is obtained (step 202). The IDDS may be obtained in a variety of ways. For example, the patient's teeth may be scanned or imaged using X-rays, three dimensional X-rays, computer-aided tomographic images or data sets, or magnetic resonance images, among others. More details on the contact or non-contact scanners are in commonly-owned and co-pending application Ser. No. 09/169,276, filed Oct. 8, 1998, the content of which is incorporated by reference.

A plaster cast of the patient's teeth is obtained by well known techniques, such as those described in Graber, *Orthodontics: Principle and Practice*, Second Edition, Saunders, Philadelphia, 1969, pp. 401-415. After the tooth casting is obtained, the casting is digitally scanned by a scanner, such as a non-contact type laser or destructive scanner or a contact-type scanner, to produce the IDDS. The data set produced by the scanner may be presented in any of a variety of digital formats to ensure compatibility with the software used to manipulate images represented by the data. In addition to the 3D image data gathered by laser scanning or destructive scanning the exposed surfaces of the teeth, a user may wish to gather data about hidden features, such as the roots of the patient's teeth and the patient's jaw bones. This information is used to build a more complete model of the patient's dentition and to show with more accuracy and precision how the teeth will respond to treatment. For example, information about the roots allows modeling of all tooth surfaces, instead of just the crowns, which in turn allows simulation of the relationships between the crowns and the roots as they move during treatment. Information about the patient's jaws and gums also enables a more accurate model of tooth movement during treatment. For example, an x-ray of the patient's jaw bones can assist in identifying any loose teeth, and an MRI can provide information about the density of the patient's gum tissue. Moreover, information about the relationship between the patient's teeth and other cranial features allows accurate alignment of the teeth with respect to the rest of the head at each of the treatment steps. Data about these hidden features may be gathered from many sources, including 2D and 3D x-ray systems, CT scanners, and magnetic resonance imaging (MRI) systems. Using this data to introduce visually hidden features to the tooth model is described in more detail below.

The IDDS is manipulated using a computer having a suitable graphical user interface (GUI) and software appropriate for viewing and modifying the images. More specific aspects of this process will be described in detail below.

Individual tooth and other components may be segmented or isolated in the model to permit their individual repositioning or removal from the digital model. After segmenting or isolating the components, the user will often reposition the tooth in the model by following a prescription or other written specification provided by the treating professional. Alternatively, the user may reposition one or more teeth based on a visual appearance or based on rules and algorithms programmed into the computer. Once the user is satisfied, the final teeth arrangement is incorporated into a final digital data set (FDDS) (step 204).

The FDDS is used to generate appliances that move the teeth in a specified sequence. First, the centers of each tooth model may be aligned using a number of methods. One method is a standard arch. Then, the teeth models are rotated until their roots are in the proper vertical position. Next, the teeth models are rotated around their vertical axis into the proper orientation. The teeth models are then observed from the side, and translated vertically into their proper vertical position. Finally, the two arches are placed together, and the teeth models moved slightly to ensure that the upper and lower arches properly mesh together. The meshing of the upper and lower arches together is visualized using a collision detection process to highlight the contacting points of the teeth.

In step 204, final positions for the upper and lower teeth in a masticatory system of a patient are determined by generating a computer representation of the masticatory system. An occlusion of the upper and lower teeth is computed from the computer representation; and a functional occlusion is computed based on interactions in the computer representation of the masticatory system. The occlusion may be determined by generating a set of ideal models of the teeth. Each ideal model in the set of ideal models is an abstract model of idealized teeth placement that is customized to the patient's teeth, as discussed below. After applying the ideal model to the computer representation, the position of the teeth is optimized to fit the ideal model. The ideal model may be specified by one or more arch forms, or may be specified using various features associated with the teeth.

Based on both the IDDS and the FDDS, a plurality of intermediate digital data sets (INTDDSs) are defined to correspond to incrementally adjusted appliances (step 206). Finally, a set of incremental position adjustment appliances are produced based on the INTDDS's and the FDDS (step 208).

Figure 3:
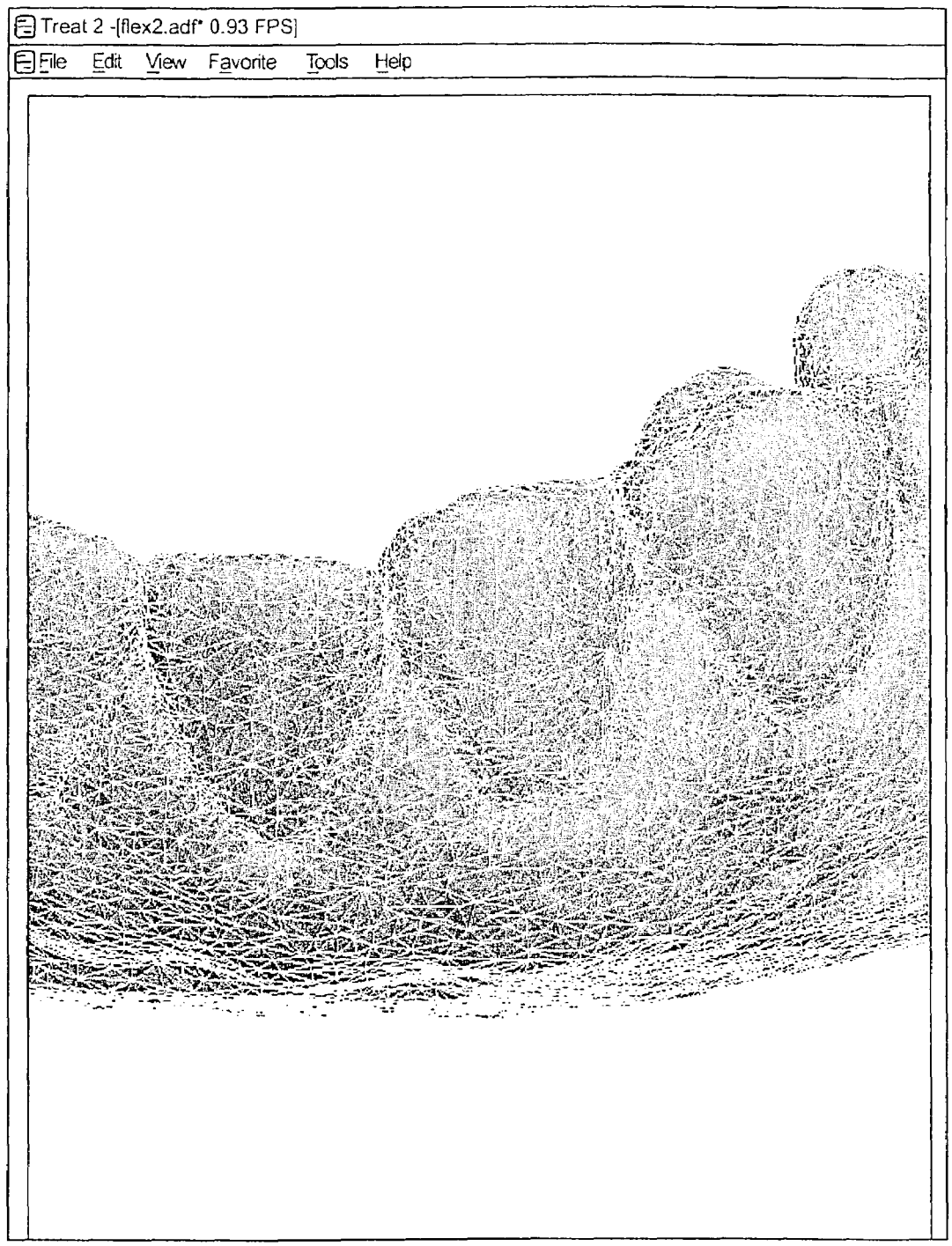
FIG. 3 is an illustration of a 3D model of teeth using triangular meshes.

FIG. 3 shows one exemplary 3D surface model of the teeth. The surface topology of a 3D model of teeth on a jaw can be modeled as a set of polygons of appropriate sizes and shapes joined at their edges. The set of polygons defining the 3D object is referred to as the "model" or "mesh" for the 3D object. In one embodiment, the polygons are triangles. In this embodiment, a triangle mesh is a piecewise linear surface with triangular faces joined along their edges.

Many types of scan data, such as that acquired by an optical scanning system, provide a 3D geometric model (e.g., a triangular surface mesh) of the teeth when acquired. Other scanning techniques, such as the destructive scanning technique described above, provide data in the form of volume elements ("voxels") that can be converted into a digital geometric model of the tooth surfaces. In one implementation, a marching cubes algorithm is applied to convert the voxels into a mesh, which can undergo a smoothing operation to reduce the jaggedness on the surfaces of the tooth model caused by the marching cubes conversion. One smoothing operation moves individual triangle vertices to positions representing the averages of connected neighborhood vertices to reduce the angles between triangles in the mesh.

The triangles in FIG. 3 form a connected graph. In this context, two nodes in a graph are connected if there is a sequence of edges that forms a path from one node to the other (ignoring the direction of the edges). Thus defined, connectivity is an equivalence relation on a graph: if triangle A is connected to triangle B and triangle B is connected to triangle C, then triangle A is connected to triangle C. A set of connected nodes is then called a patch. A graph is fully connected if it consists of a single patch. The processes discussed below keep the triangles connected.

Once a 3D model of the tooth surfaces has been constructed, models of the patient's individual teeth can be derived. In one approach, individual teeth and other components are "cut" using a cutting tool to permit individual repositioning or removal of teeth in or from the digital data. After the components are "freed", a prescription or other written specification provided by a treating professional is followed to reposition the teeth. Alternatively, the teeth may be repositioned based on the visual appearance or based on rules and algorithms programmed into the computer. Once an acceptable final arrangement has been created, the final tooth arrangement is incorporated into a final digital data set (FDDS).

Figure 4:
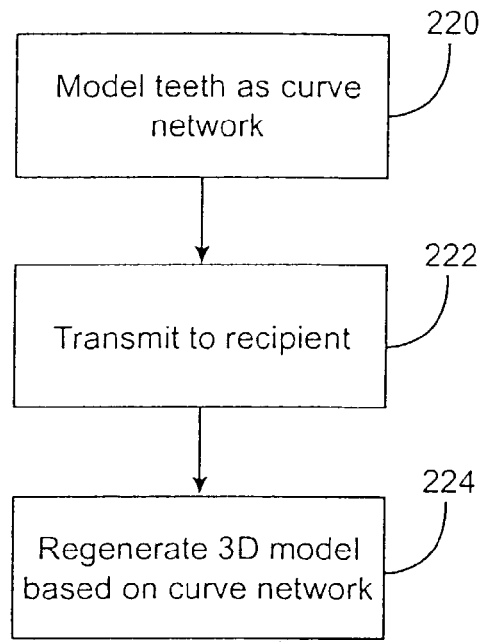
FIG. 4 shows a first embodiment of a system to represent a tooth model using a curved network.

FIG. 4 shows an embodiment of a process for communicating the 3D model of the teeth to the treating professional. Since realistic models have a large volume of data, the storage and transmission of the models can be expensive and time consuming. To reduce transmission problems arising from the large size of the 3D model, the system compresses the data associated with the model. In the embodiment of FIG. 4, the compression is done by modeling the teeth meshes as a curve network (step 220). Next, the curve network is transmitted to the treating professional (step 222). The curve network can be sent over a local area network (LAN) or a wide area network (WAN) such as the Internet. At the receiving end, once the curve network is received, the 3D model is reconstructed from the curve network for the treating professional to analyze (step 224).

Figure 5:
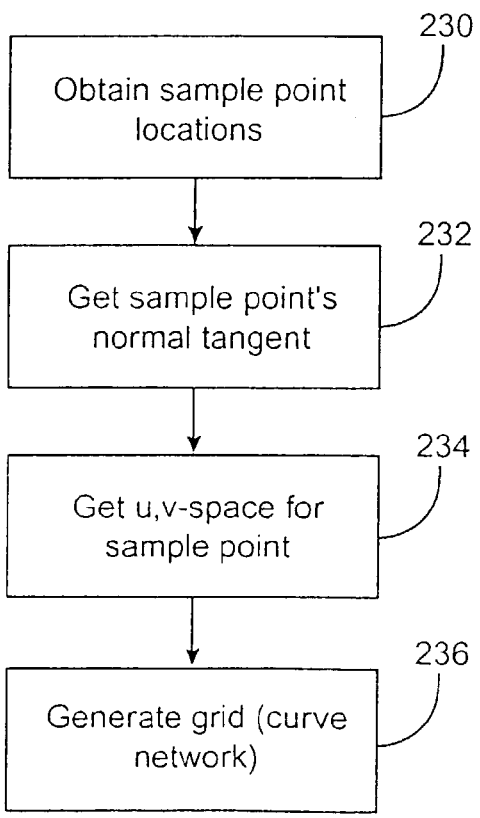
FIG. 5 is a flow chart illustrating a process for generating the curve network representative of a tooth.

The curve network generation of step 220 is shown in more detail in FIG. 5. First, the process of FIG. 5 obtains one or more sample points from the meshes of a tooth (step 230). Next, the process computes tangent values for the sample points (step 232). The sample points are converted into u, v-space (step 234). Finally, a grid or curve network is generated that satisfies the points in u, v-space (step 236). This is done by surface fitting the curve network to the original data.

In one embodiment of FIG. 5, data points are separated into groups. A U-curve with a U-knot vector is interpolated through each separate group. Next, one or more V-curves are generated by moving along each of the U-curves for a given knot value. The V-curve is formed by interpolating through these data points. The V-curves intersect the U-curves at points of constant u. A new set of U-curves that are constant in v is obtained by connecting points of constant v along the V-curves. A network of curves and its relationship to the original data points can then be generated. The only curves that are drawn are either curves of constant u or constant v, and so the regions marked out by them are rectangular in u, v-space and can be represented at patches which also mark out rectangular domains in u, v-space. A patch representation is generated from the network to arrive at a full surface description. More details on the surface fitting are discussed in pages 101-110 of Alan Watt and Mark Watt, Advanced Animation and Rendering Techniques (Addison-Wesley Publishing Company, Menlo Park, Calif.).

Figure 6A:
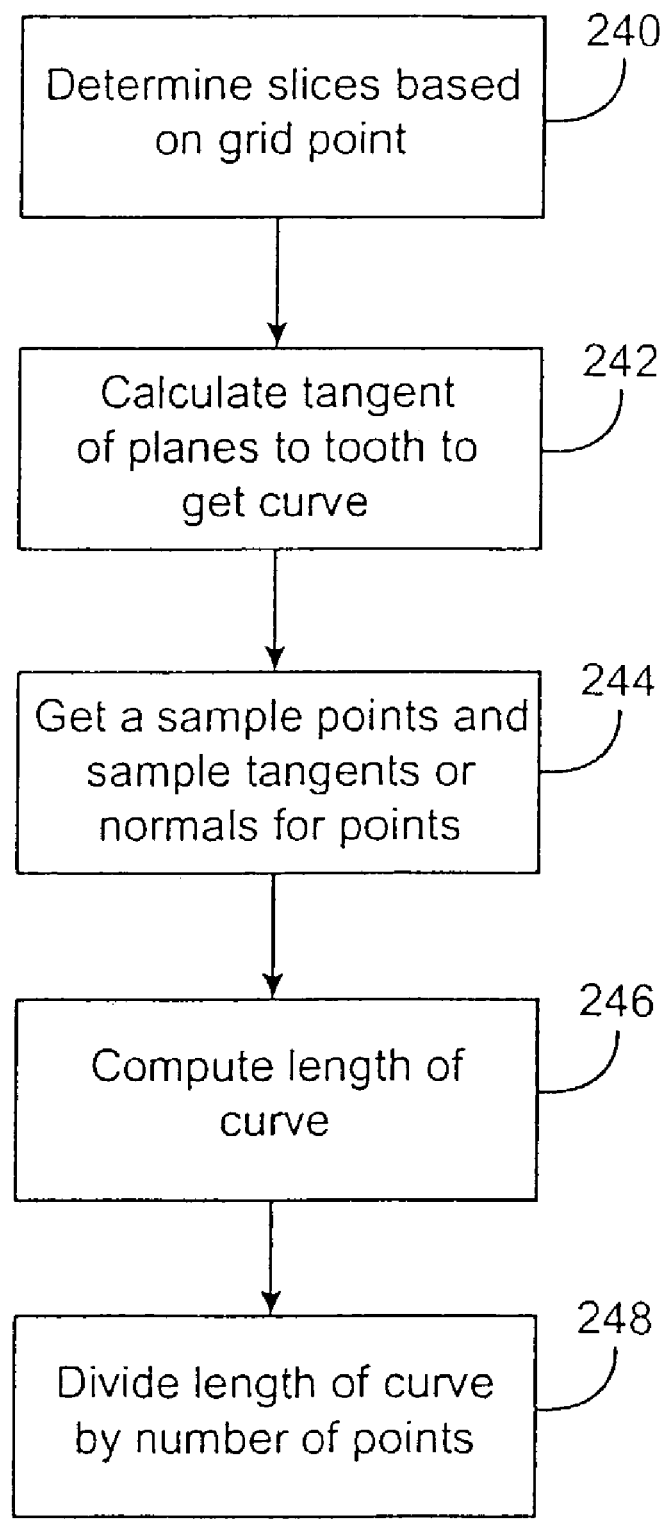
FIG. 6A is a flow chart illustrating a first process for generating an M×N network representative of a tooth.

FIG. 6A shows a flowchart for a process to create an M×N curve network associated with a tooth. First, the process determines M, the number of slices corresponding to meridian lines crossing the tooth (step 240). Next, the process calculates tangent values for a plurality of planes intersecting with the tooth to define a curve associated with one side of a slice (step 242). One or more sample points and sample tangent values for the sample points are selected (step 244) and the length of the curve is computed (step 246). Next, the process of FIG. 6A-6B divides the length of the curve N and generates points associated with the M×N curve network (step 248).

Each tooth is modeled as though it were a deformed ball. The curve network is a network of M meridian lines and N parallel lines. For each meridian line, a plane is selected to contain the meridian line. A series of points representing an intersection between the plane and the triangle mesh modeling a tooth is determined. The series of points represent a curve whose length is then determined. The length of the meridian is divided by N. If M is 20 and N is 20, a 20×20 grid of points is generated, each point being represented in 3-D. In this manner, M×N 3D points can be transmitted in place of the voluminous mesh representation of the teeth. To further reduce the size of the file, the coordinates of each point are stored using integer values rather than floating point values.

Figure 6B:
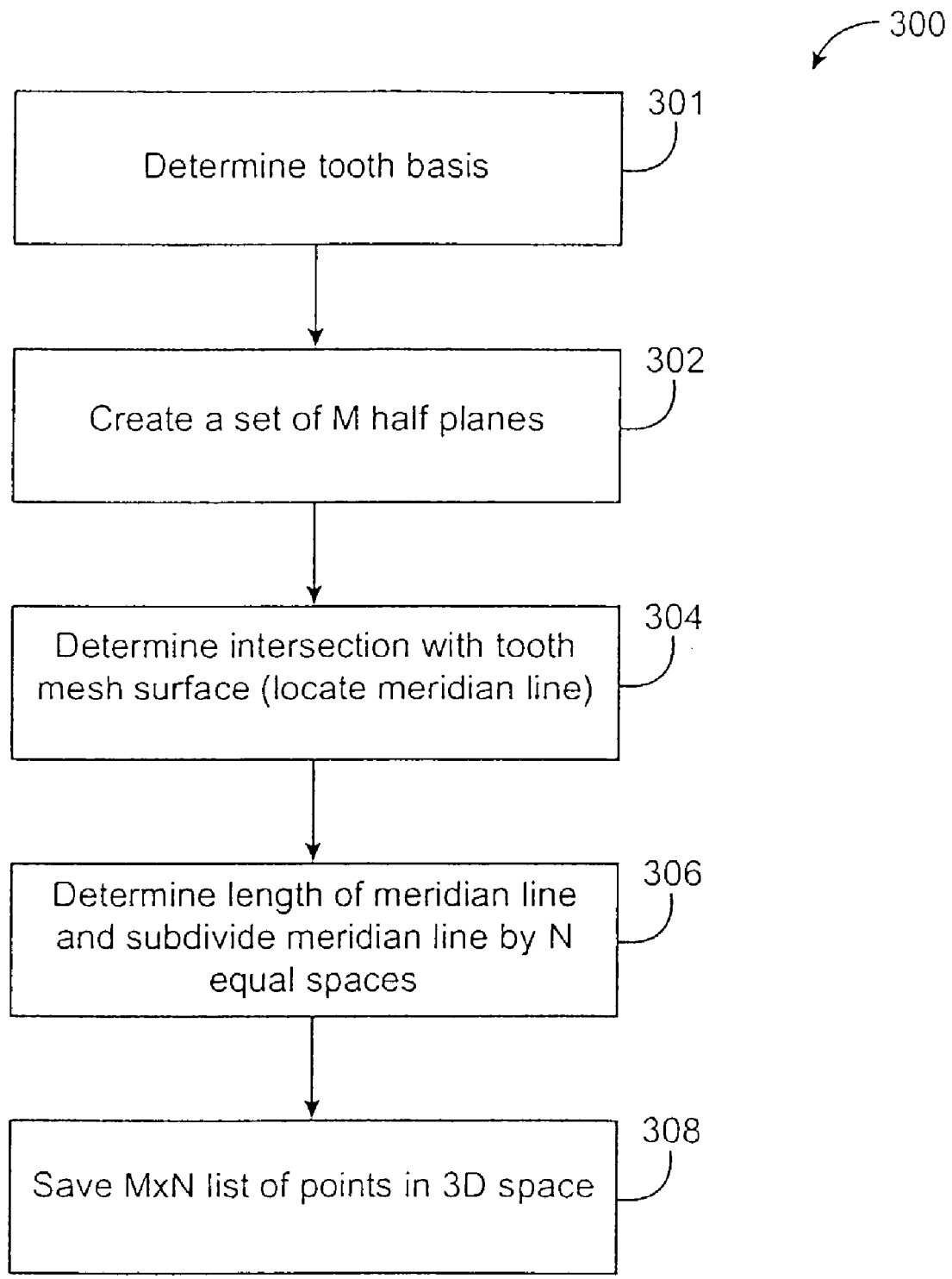
FIG. 6B is a flow chart illustrating a second process for generating an M×N network representative of a tooth.
Figure 6C:
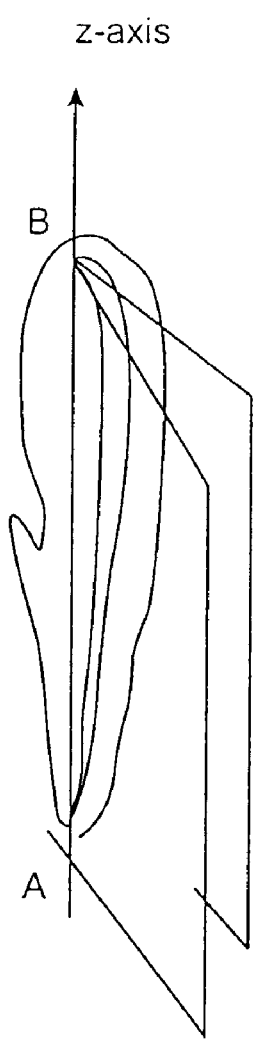
FIGS. 6C and 6D are exemplary diagrams illustrating the operation of the process of FIG. 6B on a tooth model.
Figure 6D:
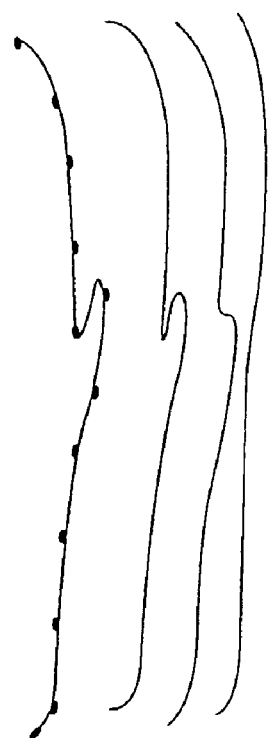

Alternatively, a second process 300 for fitting a curve network to a tooth is shown in FIG. 6B, and exemplary diagrams illustrating the operation of the process 300 on a tooth model are shown in FIGS. 6C and 6D. In FIG. 6B, during the process of creating a separate mesh for each tooth, a tooth basis is created (step 301). The tooth basis has its origin inside the tooth such as in the middle of the tooth. For reference, the z-axis points towards an occlusion surface, the y-axis points to a labial tooth surface, and the x-axis points to a mesial direction.

Next, the process 300 selects the number of meridians M. M can range between 20-40. Also, the process 300 selects the number of points on each meridian N. N typically ranges between ⅔M to M. A set of M half planes 0, . . . , (M−1) is created: each half plane goes through the tooth z-axis, and the plane i forms an angle (2*PI/M)*i with the tooth x-axis (step 302). Exemplary half planes are shown in FIG. 6C.

For each half plane, an intersection with the tooth mesh surface is determined (step 304. This intersection is a polyline that goes from the lower intersection of z-axis with the tooth surface to their upper intersection (points A and B). This line is called a meridian line.

For each meridian line, a length L is determined and S is determined as a function of L/(N−1) (step 306). From a starting point, the process 300 proceeds along the meridian line and finds points p0=A, p1, . . . , p[N−1]=B such that the point p[n+1] is at the distance S from p[n] along the meridian. Eventually, an M*N list of points in 3D space is generated and saved (step 308). The points can be saved as short integer values rather than floating point values.

The data is saved and sent to a treating professional. To reconstruct a surface, the grid of M by N points is used to generate a surface that closely resembles a tooth. Although 20 is used in one embodiment, other values for M or N can be 30 or 40.

To reconstruct a surface from a M*N grid of points, a Hermit spline is specified that maps a rectangle [0, M]*[0, N] in (u, v) parameter plane into 3D space. The Hermit spline is a bicubic 3D function on each [m, m+1]*[n, n+1] square in parameter plane. The Hermit spline F is a smooth continued function on the [0, M]*[0, N] rectangle. When restricted to any [m, m+1]*[n, n+1] unit square, the spline is a bicubic 3D function. The restriction of F onto [m, m+1]*[n, n+1] square is denoted by f (omitting the indices (m, n) that should signify that functions f are different on different squares).

The function forms a continuous smooth function on the [0, M]*[0, N] rectangle.

To determine a Hermit spline, 3D values F, two derivatives dF/du, dF/dv, and the second mixed derivative d2F/dudv in each nod point (m, n). Thus for each bicubic function f on [m, m+1]*[n, n+1] square, 3D values f, two derivatives df/du, df/dv, and the second mixed derivative d2f/dudv are generated for the four square corners (m, n), (m+1, n), (m, n+1), (m+1, n+1). A unique 3D bicubic function is completely determined by those values. The bicubic functions on the next squares are smoothly connected because the values and derivatives are the same on the common side.

The 3D values F, two derivatives dF/du, dF/dv, and the second mixed derivative d2F/dudv in the nod points (m, n) are specified as follows:

F(m, n)=(m, n)-th grid point P(m, n);
dF/du(m, n)=0.5*(P(m+1, n)−P(m−1, n));
dF/dv(m, n)=0.5*(P(m, n+1)−P(m, n−1));
2F/dudv(m, n)=0.

After the Hermit spline on the rectangle [0, M]* [0, N] is determined, its values in the more dense grid of points K*L are computed to derive a K*L grid of 3D points. Each of the four points (k, 1), (k+1, k), (k, 1+1), (k+1, 1+1) are associated with two triangles: {(k, 1), (k+1, k), (k, 1+1)} and {(k, 1+1), (k+1, 1+1), (k, 1)}. In this way, 2*K*L triangles are generated that are then rendered as a reconstructed tooth.

Figure 7:
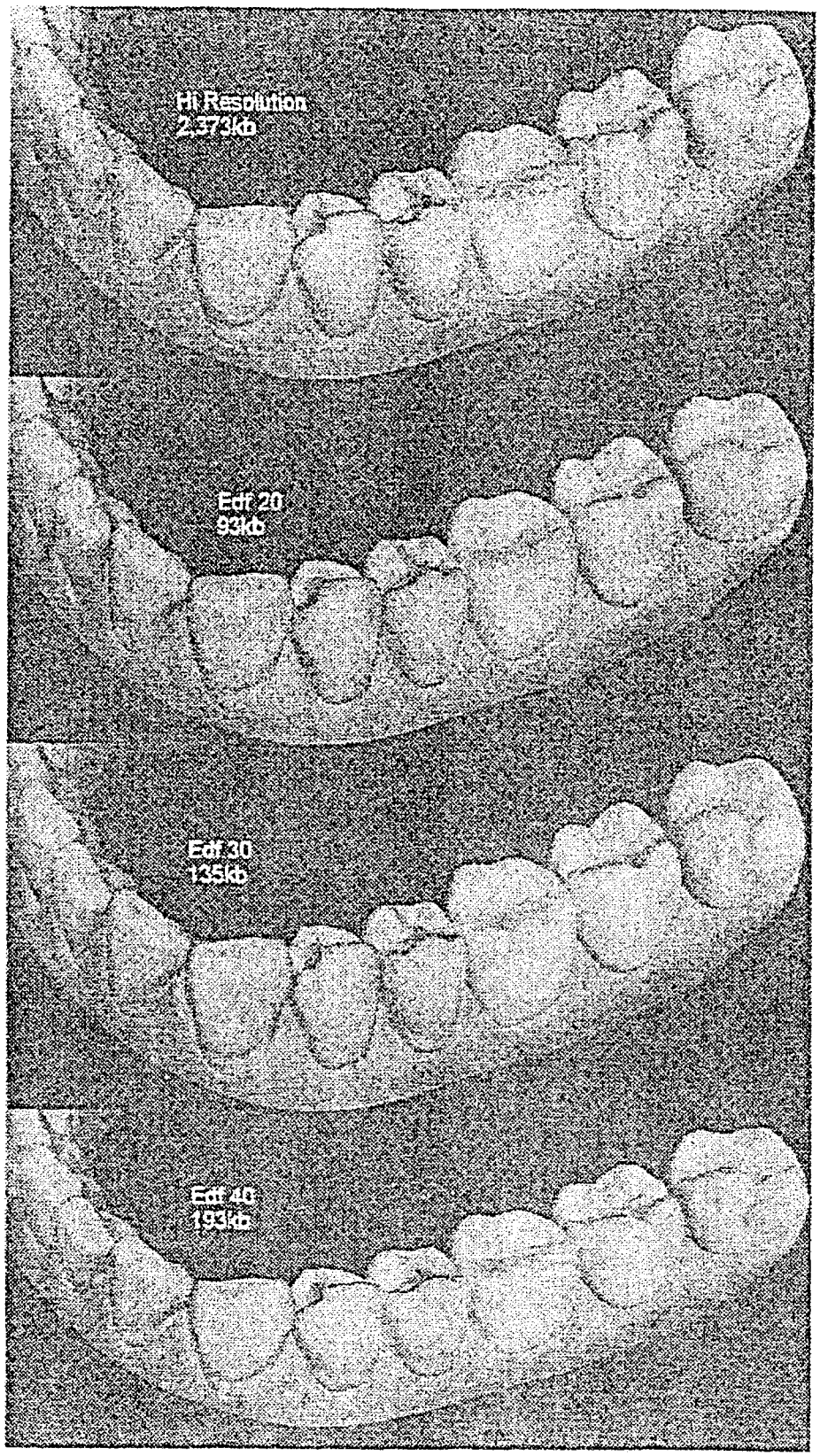
FIG. 7 shows an original high-resolution teeth model and various compressed versions of the teeth model using the processes of FIGS. 5-6D.

FIG. 7 shows an original high-resolution model 250 of a group of lower teeth and various compressed models of the high-resolution model of the teeth. The original high-resolution model requires 2.373 megabytes of data. In comparison, a 20×20 model 252 requires 93 kilobytes, a 30×30 model 254 requires 135 kilobytes, and a 40×40 model requires 193 kilobytes. The reduction in the size of the file reduces the storage as well as transmission requirements while maintaining good quality. At least one orthodontist had noted that the 30×30 model is, for his application, as good as the original high resolution model 250 in developing a treatment plan.

Figure 8:
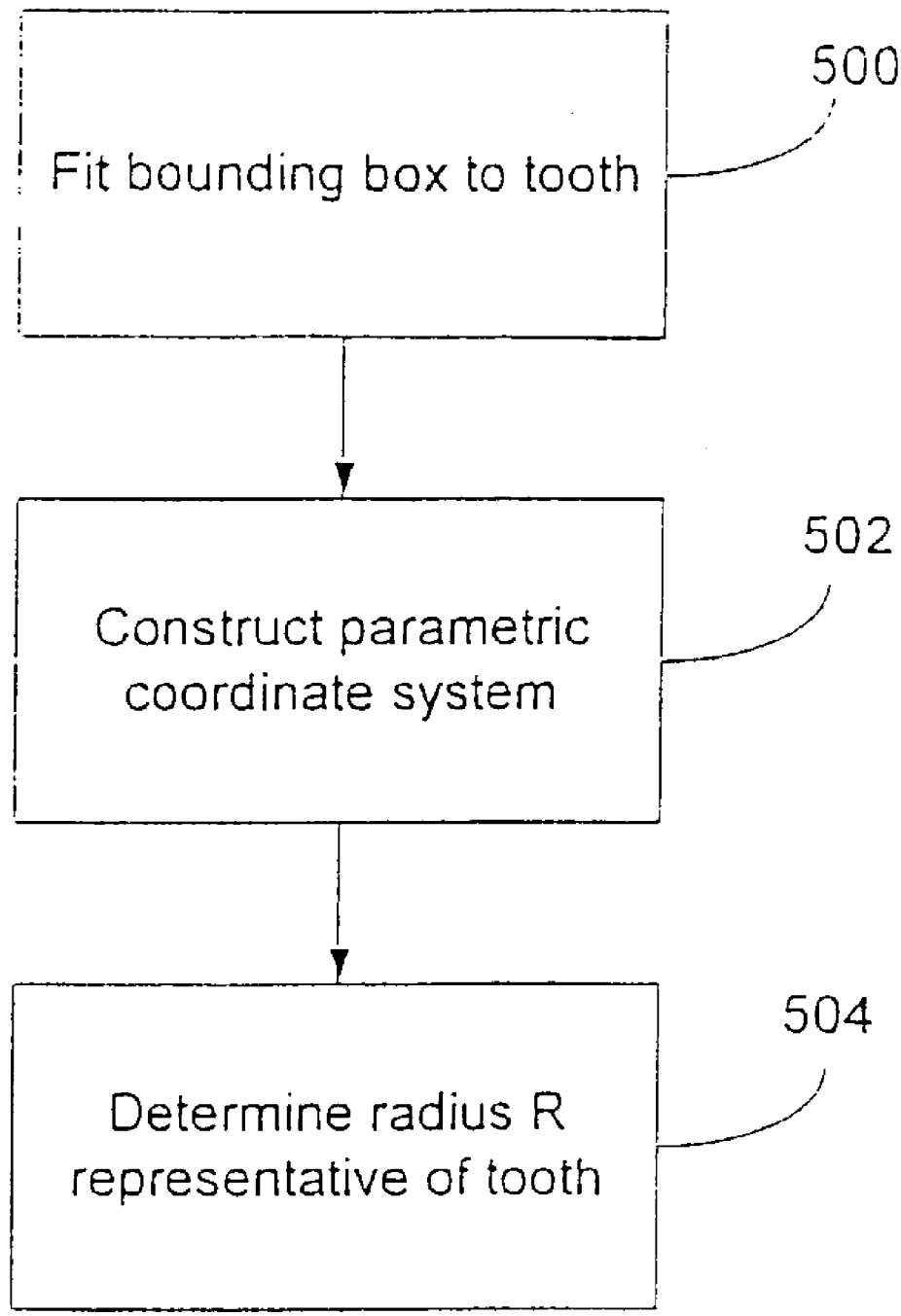
FIG. 8 shows a second embodiment of a system to represent a tooth model using a parametric coordinate system.

FIG. 8 shows another embodiment that uses a curved coordinate system to perform parametric ($\phi$, $\theta$, r) to 3D transformations. The process first fits a box into a tooth (step 500). The fitting of the box allows parameters of the curved coordinate system to be determined more accurately.

A parametric coordinate system is constructed (step 502). The coordinate system specifies the conversion of a point P($\phi$,$\theta$, r) into 3D space. $\Phi$ ranges from 0 to $2\pi$; $\theta$ ranges from 0 to $\pi$; and r ranges from 0 to positive infinity.

The phi theta $\phi$, $\theta$ space is represented as a regular grid. The step of the grid is determined using the following formulas $$d\_\phi = 2*\pi/\phi\_Resolution \text{ and}$$

$$d\_\theta = \pi/\theta\_Resolution.$$

In general, the coordinate system can be specified using other parameters, and should satisfy several requirements:

1. The coordinates should parameterize the entire 3D space, or the 3D space except a small set inside the tooth.
2. Curves phi=const and theta=const should be linear functions of R (rays). The following formula must be used V(x,y,z)=P(phi, theta)+R*Dir(phi, theta).
3. Coordinate system should provide one-to-one mapping so that rays for different phi and theta do not intersect.
4. Solution should account for different types of teeth.
5. Coordinate system should be simple enough to implement inverse transformation, from 3D space to parametric coordinates. It's desired that sets phi=const be planes.

In one embodiment, the ($\phi,\theta$, r)->3D transformation is done with the following equations:

$$phi \in [0, 2\pi].$$

$$theta \in [0, \pi];$$

$$R \in [0, \text{positive infinity}).$$

$$V(x,y,z) = P(phi, theta) + R*\text{Direction}(phi, theta)$$

P and Direction functions should be selected to minimize the deviation between the original tooth model and the parametric surface. The formulas for P and Direction may be different for incisors and molars. In one embodiment, the formulas are as follows:

1. For incisor teeth $$P.x = 0;$$

$$P.y = Y\text{Size}*\sin(phi);$$

$$p.z = Z\text{Size}*(1 - 2*theta/P_i);$$

$$\text{Direction}.x = \sin(theta)*\cos(phi);$$

$$\text{Direction}.y = \sin(theta)*\sin(phi);$$

$$\text{Direction}.z = \cos(theta);$$

For molars and other types of teeth:

$$P.x = X\text{Size}*\sin(theta)*[1 + \sin^2(2phi)]\cos(phi);$$

$$P.y = Y\text{Size}*\sin(theta)*[1 + \sin^2(2phi)]\sin(phi);$$

$$p.z = Z\text{Size}*(1 - 2*theta/P_i);$$

$$\text{Direction}.x = \sin(theta)*\cos(phi);$$

$$\text{Direction}.y = \sin(theta)*\sin(phi);$$

$$\text{Direction}.z = \cos(theta);$$

Additionally, a radius R representative of the tooth is constructed (step 504). The radius determination is shown in more detail in FIG. 9.

Figure 9:
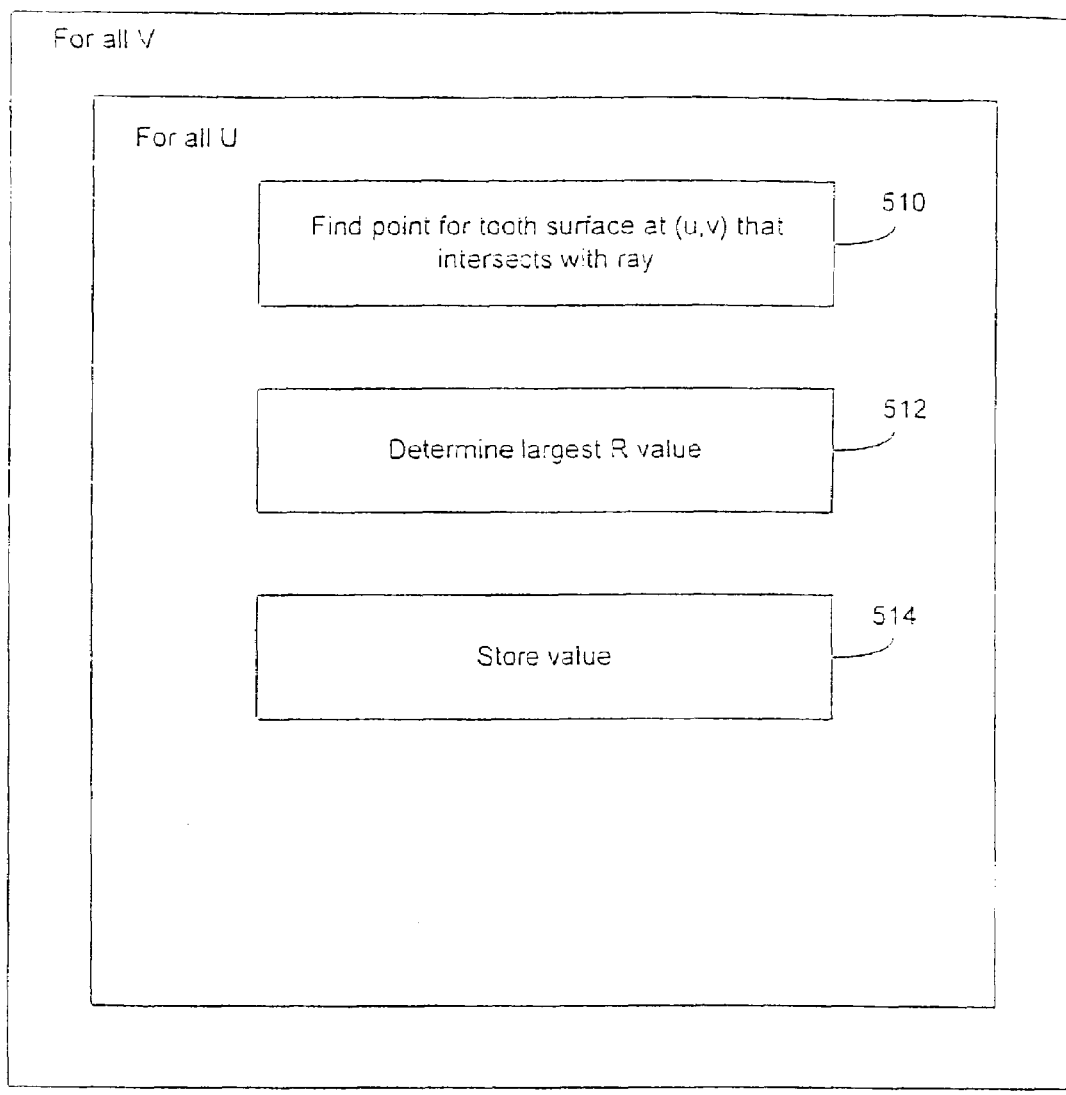
FIG. 9 shows a process for determining a value representative of a tooth.

The process of FIG. 9 determines R by stepping through each phi and each theta on the grid in the Phi x Theta space and computes the following. First, the process determines a point on the tooth surface at the point P ($\phi,\theta$) that intersects with a ray originating at P aiming at a destination direction specified by Direction (step 510).

Next, the process of FIG. 9 determines the largest R-value for all points of intersection of the ray with the tooth (step 512). The value determined in step 512 is stored in a table (step 514), and the process is iterated until all phi and theta values have been processed. In one embodiment, for each value stored in the nodes of Phi x Theta grid, only one byte of data is saved to disk. Minimum and maximum values of R are computed. The interval [minR, maxR] is divided into 255 parts. Any R may be approximated using the following formula $$\text{BYTE } b = (\text{BYTE})(255*(R-\text{min}R)/(\text{max}R-\text{min}R));$$

Since maxR−minR is approximately 5-6 mm for human teeth, the error introduced by this formula is 5/255 mm=0.02 mm.

The collision detection or the determination of the intersection line between two surfaces is efficient. During this process, the embodiment computes the elevation of all grid points in one tooth surface over the other one. If two next points in the grid have different sign elevations, then the segment connecting these points intersects the surface. The segment is approximately divided by the surface into parts proportional to the elevation in its ends. The intersection points on the sides of one grid cell may be connected according to the elevation signs in the vertices to generate an intersection line. This embodiment may be speeded up by first computing elevation values for sub-grid (2*2 or 3*3) of points.

In some applications, tooth penetration may be estimated as the maximum of (minus) elevation of the grid points having a negative elevation. In other applications the penetration may be estimated as (minus) sum of negative elevation. Also, each negative elevation may be multiplied by the cell area. In the latter case, the result is equivalent to the volume of the 3D bodies intersection. Due to the geometry representation, certain minor collisions with small penetrations (smaller than the treatment precision) may occur and these small collisions are ignored by the system.

Given a cell size and the angle between cells, the system can estimate how much a tooth may penetrate into another tooth if all its vertices are outside. The penetration may be significant only if there is a sharp outer angle. When the vertices are found with a small elevation, the mesh in those elevated areas are subdivided. (This is similar to starting with 3*3 mesh, and taking a smaller mesh in close areas only.)

When a user drags a tooth model to move it, teeth penetrations are approximately computed, without subdivisions. When a user releases the tooth model, the penetration can be computed more precisely. If a collision exists, the tooth can be moved a small distance to avoid collision.

The teeth penetration and "distance" (positive elevation) between two teeth are estimated quickly. When the tooth movements are small, the elevation is approximately proportional to the tooth movement (the functions are locally linear), so a touching position (a position with zero elevation) can be determined quickly.

Pseudo-code for the processes of FIGS. 8 and 9 is shown below:

EDF2 ConvertTooth (tooth, resolutionPhi, resolutionTheta)
Construct the biggest box that is inside the tooth in the current basis. The box sides must be parallel to coordinate planes(XY, YZ and XY). Move the center of the coordinate system to the center of the box.

Use the sides of the bounding box to construct the parameters of the coordinate system.

$$X\text{Size} = 0.8*(\text{Box.getMax}().x - \text{Box.getMin}().x)/4;$$

$$Y\text{Size} = 0.8*(\text{Box.getMax}().y - \text{Box.getMin}().y)/4;$$

$$Z\text{Size} = 0.8*(\text{Box.getMax}().z - \text{Box.getMin}().z)/4;$$

Sometimes XSize may be made equal to YSize and to min(XSize, YSize). This ensures that the set of 3D points "phi=const" is a plane.

For(theta=0; theta<resolutionTheta; theta++)
For(phi=0; phi<resolutionPhi; phi++)
 1. Find a point on the tooth surface that intersects with the ray for given u and v.
 2. Using that point calculate the R value.
 R=‖Point−P($\phi$,$\theta$)‖, using formula (1)
 Since the ray may intersect the surface in more than one point, select the point with the largest R to not make the tooth smaller. This situation should not happen at all, if the coordinate system is "good" for the tooth, but it happens sometimes in small cavities or in cut regions.
 3. Store that value in the table.

The processes of FIGS. 8-9 parameterize substantially all 3D space, less a small region inside the tooth. The result is a computationally simple formula that performs (u,v,r)->3D. The inverse mapping 3D->(u,v,r) should also exist and should not involve much computation as well. The process represents the surface in parametric coordinates as an explicit smooth function (smooth—continuous first derivatives) of phi an theta, such as R=F(phi, theta). The compression reduces disk space requirement and increases transmission speed to a clinician.

Moreover, for every 3D point P, the system can easily detect whether the point is inside the tooth for a fast collision detection. It can be accomplished in the following way:
 1. Convert P into parametric form (phi, theta, R).
 2. For the above phi and theta find Rt of the tooth surface, for example, using bilinear interpolation.
 3. If R>Rt, the point is outside the tooth.

Although the above parametric techniques can be used to compress the storage size of a mesh model of a tooth, other techniques can be used. In another embodiment, decimation operations can be applied to the mesh of teeth to eliminate data points, which improves processing speed. After the smoothing and decimation operation have been performed, an error value is calculated based on the differences between the resulting mesh and the original mesh or the original data, and the error is compared to an acceptable threshold value. The smoothing and decimation operations are applied to the mesh once again if the error does not exceed the acceptable value. The last set of mesh data that satisfies the threshold is stored as the tooth model.

Additionally, the mesh model can be simplified by removing unwanted or unnecessary sections of the model to increase data processing speed and enhance the visual display. Unnecessary sections include those not needed for creation of the tooth-repositioning appliance. The removal of these unwanted sections reduces the complexity and size of the digital data set, thus accelerating manipulations of the data set and other operations. After the user instructs the software to erase unwanted sections, all triangles within the box set by the user are removed and the border triangles are modified to leave a smooth, linear border. The software deletes all of the triangles within the box and clips all triangles that cross the border of the box. This requires generating new vertices on the border of the box. The holes created in the model at the faces of the box are retriangulated and closed using the newly created vertices.

In alternative embodiments, the computer automatically simplifies the digital model by performing the user-oriented functions described above. The computer applies knowledge of orthodontic relevance to determine which portions of the digital model are unnecessary for image manipulation.

In another embodiment, data associated with the 3D model includes features can be compressed based on observed characteristics of the tooth surfaces. For example, the system can use the curvature of a particular molar between the tips of the cusps and the gumline to predict the shape of the roots for that molar. Models of typical root and crown shapes also can be used to predict the shape of the tooth. The information used to arrive at the predicted shapes can be used in lieu of the original data, thus effecting data compression.

Other feature detection techniques use databases of known cases or statistical information against which a particular 3D image is matched using conventional image pattern matching and data fitting techniques. One such technique, known as "Maximum a posteriori" (MAP), uses prior images to model pixel values corresponding to distinct object types (classes) as independent random variables with normal (Gaussian) distributions whose parameters (mean and variance) are selected empirically. For each class, a histogram profile is created based on a Gaussian distribution with the specified mean and variance. The prior images supply for each pixel and each class the probability that the pixel belongs to the class, a measure which reflects the relative frequency of each class. Applying Bayes' Rule to each class, the pixel values in the input image are scaled according to the prior probabilities, then by the distribution function. The result is a posterior probability that each pixel belongs to each class. The Maximum a posteriori (MAP) approach then selects for each pixel the class with the highest posterior probability.

Once downloaded to a remote workstation, a treating clinician is able to view a patient's treatment plan and alter or comment on the plan. The client viewer application is implemented in a computer program installed locally on a client computer at the clinician's site. In one implementation, the viewer program downloads a data file from a remote host, such as a file transfer protocol (FTP) server maintained by the treatment plan designer, which can be accessed either through direct connection or through a computer network, such as the World Wide Web. The viewer program uses the downloaded file to present the treatment plan graphically to the clinician. The viewer program also can be used by the treatment plan designer at the host site to view images of a patient's teeth.

3-D images of various orthodontic views can then be rendered after the compressed data of the teeth has been received. In this process, an origin point, or "look from" point associated with a camera view is generated. Next, a "look at" point or a focus point associated with the camera view is determined. In this system, the line from LookFromPoint to LookAtPoint defines the direction the camera is shooting at. Additionally, a camera Z vector, or up vector, is determined.

Figure 10:
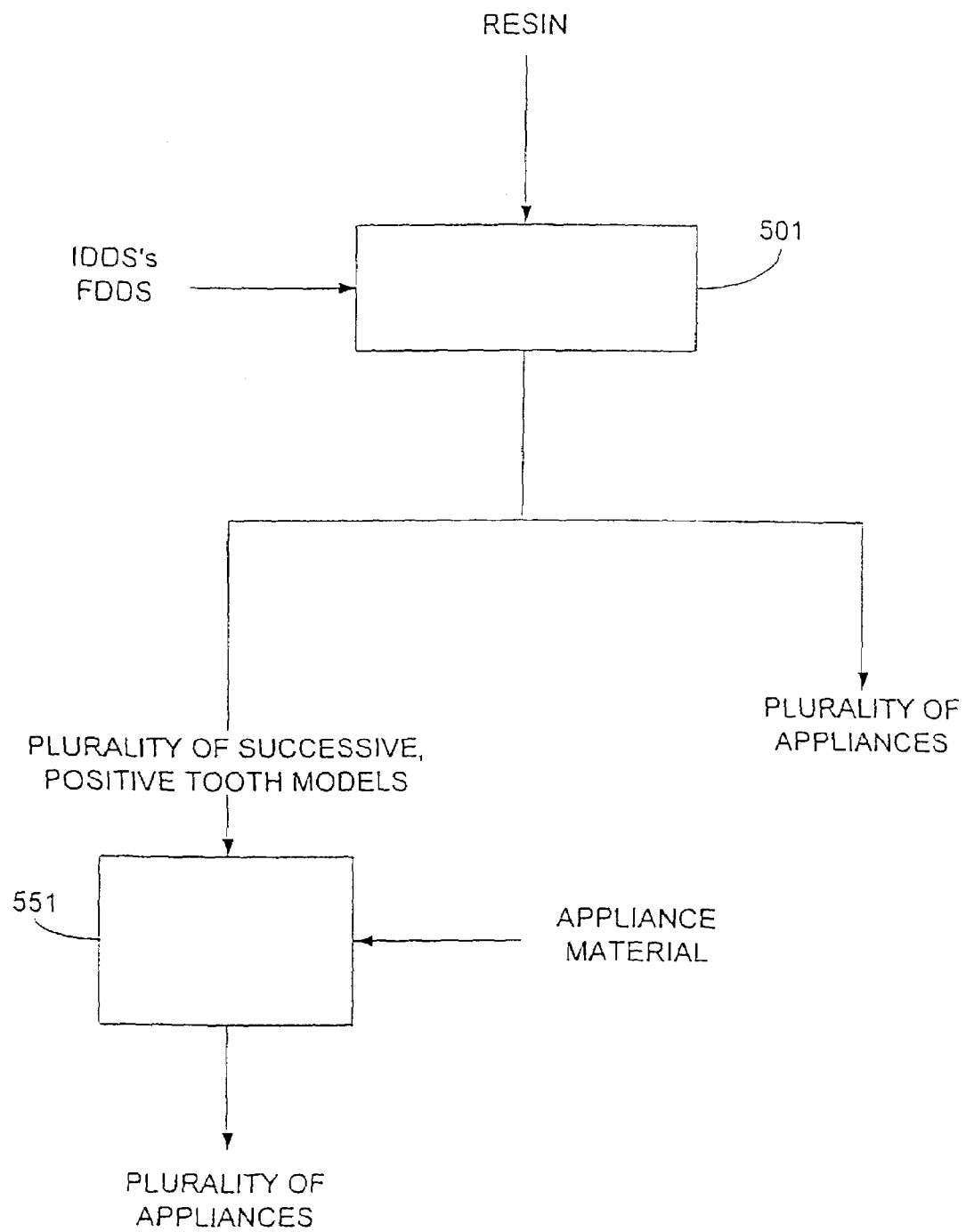
FIG. 10 shows a diagram of a system for fabricating appliances.

Pseudo code for generating various orthodontic views is shown below. With reference to the pseudo code, the code defines a boundingbox of one mold (2 arches) which is the smallest cube containing the molds geometry. Other settings associated with the bounding box include:
 Z_Axis: point from lower to upper,
 Y_Axis: point from inside mouse to front teeth (incisors)
 X_Axis: point from center to left.
 FieldOfView: is the open angle, it corresponding to lens
 HalffieldOfView: FieldOfView*0.5
 MoldCenter: Center of the BoundingBox
 X_Length: BoundingBox X dimension
 Y_Length: BoundingBox X dimension
 Z_Length: BoundingBox X dimension
 X_MIN: minimum X value of the BoundingBox i.e. right most surface cube X value.
 X_MAX: maximum X value of the BoundingBox
 Y_MIN: minimum Y value of the BoundingBox
 Y_MAX: maximum Y value of the BoundingBox
 Z_MIN: minimum Z value of the BoundingBox
 Z_MAX: maximum Z value of the BoundingBox Right Buccal Overjet
  CameraLookFromPoint:
  X=0.5*MoldCenter.X+0.5*X_Max+0.25* MAX (Y_Length, Z_Length)/tan(HalfFieldOfView);
  Y=MoldCenter.Y
  Z=MoldCenter.Z−0.25*MAX(Y_Length, Z_Length)/tan (HalfFieldOfView);
  CameraLookAtPoint:
  X=MoldCenter.X+0.25*X_Length;
  Y MoldCenter.Y;
  Z=MoldCenter.Z;
  CameraUpVector: ZAxis;

Anterior Overjet
  CameraLookFromPoint:
  X=MoldCenter.X;
  Y=0.5*MoldCenter.Y+0.5*Y_Max+0.25* MAX (X_Length, Z_Length)/tan(HalfFieldOfView);
  Z=MoldCenter.Z−0.25* MAX(X_Length, Z_Length)/tan (HalfFieldOfView);
  CameraLookAtPoint:
  X=MoldCenter.X;
  Y=MoldCenter.Y+0.25*Y_Length;
  Z=MoldCenter.Z;
  CameraUpVector: ZAxis;

Left Buccal Overjet
  CameraLookFromPoint:
  X=0.5*MoldCenter.X+0.5*X_Min−0.25*MAX (Y_Length, Z_Length)/tan(HalfFieldOfView);
  Y=MoldCenter.Y;
  Z=MoldCenter.Z−0.25*MAX(Y_Length, Z_Length)/tan (HalfFieldOfView);
  CameraLookAtPoint:
  X=MoldCenter.X−0.25*X_Length;
  Y=MoldCenter.Y;
  Z=MoldCenter.Z;
  CameraUpVector: ZAxis;

Left Distal_Molar
  CameraLookFromPoint:
  X=MoldCenter.X−0.25*X_Length;
  Y=Y_Min−0.25*MAX(X_Length, Z_Length)/tan (HalfFieldOfView);
  Z=MoldCenter.Z;
  CameraLookAtPoint:
  X=MoldCenter.X−0.25*X_Length;
  Y=MoldCenter.Y;
  Z=MoldCenter.Z;
  CameraUpVector: ZAxis;

Left Lingual
  CameraLookFromPoint:
  X=MoldCenter.X+0.125*X_Length;
  Y=MoldCenter.Y;
  Z=MoldCenter.Z;
  CameraLookAtPoint:
  X=MoldCenter.X−0.25*X_Length;
  Y=MoldCenter.Y;
  Z=MoldCenter.Z;
  CameraUpVector: ZAxis;

Lingual Incisor
  CameraLookFromPoint:
  X=MoldCenter.X;
  Y=MoldCenter.Y;
  Z=MoldCenter.Z;
  CameraLookAtPoint:
  X=MoldCenter.X;
  Y=MoldCenter.Y+0.25*Y_Length;
  Z=MoldCenter.Z;
  CameraUpVector: ZAxis;

Right Lingual
  CameraLookFromPoint:
  X=MoldCenter.X+0.125*X_Length;
  Y=MoldCenter.Y;
  Z=MoldCenter.Z;
  CameraLookAtPoint:
  X=MoldCenter.X+0.25*X_Length;
  Y=MoldCenter.Y;
  Z=MoldCenter.Z
  CameraUpVector: ZAxis;

Right Distal Molar
  CameraLookFromPoint:
  X=MoldCenter.X+0.25*X_Length;
  Y=Y_MIN−0.25*MAX(X_Length, Z_Length)/tan (HalfFieldOfView);
  Z=MoldCenter.Z;
  CameraLookAtPoint:
  X=MoldCenter.X+0.25*X_Length;
  Y=MoldCenter.Y;
  Z=MoldCenter.Z;
  CameraUpVector: ZAxis;

Once the intermediate and final data sets have been created and reviewed by an orthodontist or suitably trained person, the appliances may be fabricated as illustrated in FIG. 10. Common fabrication methods employ a rapid prototyping device 501 such as a stereolithography machine. A particularly suitable rapid prototyping machine is Model SLA-250/50 available from 3D System, Valencia, Calif. The rapid prototyping machine 501 selectively hardens a liquid or other non-hardened resin into a three-dimensional structure which can be separated from the remaining non-hardened resin, washed, and used either directly as the appliance or indirectly as a mold for producing the appliance. The prototyping machine 501 receives the individual digital data sets and produces one structure corresponding to each of the desired appliances. Generally, because the rapid prototyping machine 501 may utilize a resin having non-optimum mechanical properties and which may not be generally acceptable for patient use, the prototyping machine typically is used to produce molds which are, in effect, positive tooth models of each successive stage of the treatment. After the positive models are prepared, a conventional pressure or vacuum molding machine is used to produce the appliances from a more suitable material, such as 0.03 inch thermal forming dental material, available from Tru-Tain Plastics, Rochester, Minn. 55902. Suitable pressure molding equipment is available under the trade name BIOSTAR from Great Lakes Orthodontics, Ltd., Tonawanda, N.Y. 14150. The molding machine 551 produces each of the appliances directly from the positive tooth model and the desired material. Suitable vacuum molding machines are available from Raintree Essix, Inc.

After production, the appliances can be supplied to the treating professional all at one time. The appliances are marked in some manner, typically by sequential numbering directly on the appliances or on tags, pouches, or other items which are affixed to or which enclose each appliance, to indicate their order of use. Optionally, written instructions may accompany the system which set forth that the patient is to wear the individual appliances in the order marked on the appliances or elsewhere in the packaging. Use of the appliances in such a manner will reposition the patient's teeth progressively toward the final tooth arrangement.

Because a patient's teeth may respond differently than originally expected, the treating clinician may wish to evaluate the patient's progress during the course of treatment. The system can also do this automatically, starting from the newly measured in-course dentition. If the patient's teeth do not progress as planned, the clinician can revise the treatment plan as necessary to bring the patient's treatment back on course or to design an alternative treatment plan. The clinician may provide comments, oral or written, for use in revising the treatment plan. The clinician also can form another set of plaster castings of the patient's teeth for digital imaging and manipulation. The clinician may wish to limit initial aligner production to only a few aligners, delaying production on subsequent aligners until the patient's progress has been evaluated.

Figure 11:
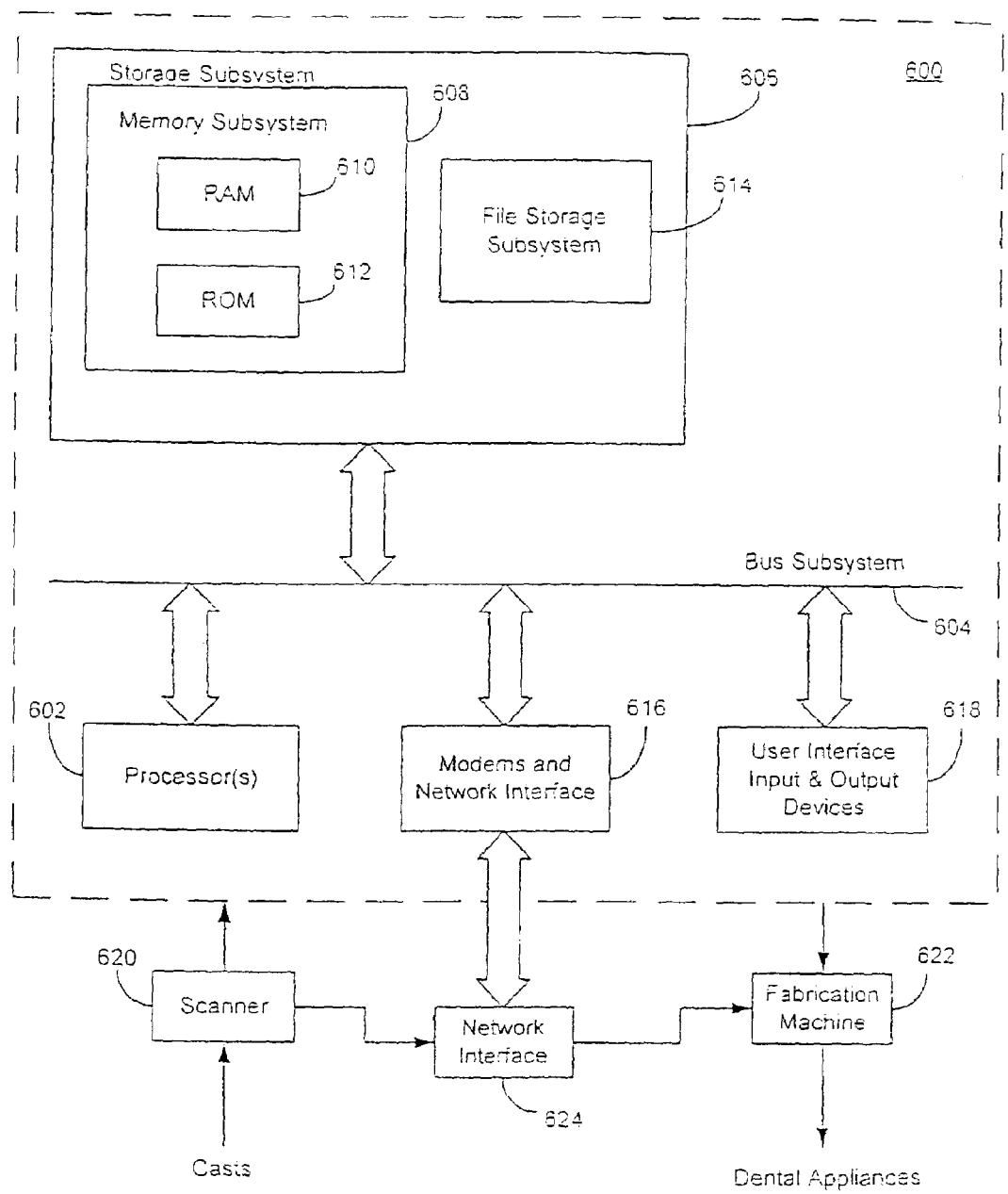
FIG. 11 is a block diagram of a data processing system to develop orthodontic treatment plans.

FIG. 11 is a simplified block diagram of a data processing system 600 that may be used to develop orthodontic treatment plans. The data processing system 600 typically includes at least one processor 602 that communicates with a number of peripheral devices via bus subsystem 604. These peripheral devices typically include a storage subsystem 606 (memory subsystem 608 and file storage subsystem 614), a set of user interface input and output devices 618, and an interface to outside networks 616, including the public switched telephone network. This interface is shown schematically as "Modems and Network Interface" block 616, and is coupled to corresponding interface devices in other data processing systems via communication network interface 624. Data processing system 600 could be a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touch-pad, or graphics tablet, or a direct pointing device such as a touch-screen incorporated into the display, or a three dimensional pointing device, such as the gyroscopic pointing device described in U.S. Pat. No. 5,440,326, other types of user interface input devices, such as voice recognition systems, can also be used.

User interface output devices typically include a printer and a display subsystem, which includes a display controller and a display device coupled to the controller. The display device may be a cathode ray tube (CRT), a flat-panel device such as a liquid crystal display (LCD), or a projection device. The display subsystem may also provide non-visual display such as audio output.

Storage subsystem 606 maintains the basic required programming and data constructs. The program modules discussed above are typically stored in storage subsystem 606. Storage subsystem 606 typically comprises memory subsystem 608 and file storage subsystem 614.

Memory subsystem 608 typically includes a number of memories including a main random access memory (RAM) 610 for storage of instructions and data during program execution and a read only memory (ROM) 612 in which fixed instructions are stored. In the case of Macintosh-compatible personal computers the ROM would include portions of the operating system; in the case of IBM-compatible personal computers, this would include the BIOS (basic input/output system).

File storage subsystem 614 provides persistent (non-volatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus sub-system" is used generically so as to include any mechanism for letting the various components and subsystems communicate with each other as intended. With the exception of the input devices and the display, the other components need not be at the same physical location. Thus, for example, portions of the file storage system could be connected via various local-area or wide-area network media, including telephone lines. Similarly, the input devices and display need not be at the same location as the processor, although it is anticipated that personal computers and workstations typically will be used.

Bus subsystem 604 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 620 is responsible for scanning casts of the patient's teeth obtained either from the patient or from an orthodontist and providing the scanned digital data set information to data processing system 600 for further processing. In a distributed environment, scanner 620 may be located at a remote location and communicate scanned digital data set information to data processing system 600 via network interface 624.

Fabrication machine 622 fabricates dental appliances based on intermediate and final data set information received from data processing system 600. In a distributed environment, fabrication machine 622 may be located at a remote location and receive data set information from data processing system 600 via network interface 624.

The invention has been described in terms of particular embodiments. Other embodiments are within the scope of the following claims. For example, the three-dimensional scanning techniques described above may be used to analyze material characteristics, such as shrinkage and expansion, of the materials that form the tooth castings and the aligners. Also, the 3D tooth models and the graphical interface described above may be used to assist clinicians that treat patients with conventional braces or other conventional orthodontic appliances, in which case the constraints applied to tooth movement would be modified accordingly. Moreover, the tooth models may be posted on a hypertext transfer protocol (http) web site for limited access by the corresponding patients and treating clinicians.

What is claimed is:

1. A computer-implemented method for generating a computer model of one or more teeth, comprising:
    receiving as input a digital data set of meshes representing the teeth; creating a parametric representation of the teeth from the digital data set, wherein the parametric representation comprises exposed tooth surface image data and unexposed tooth surface image data and further provides compression of the digital data set, the parametric representation comprising:

a curved coordinate system with mappings to and from a (u, v) space wherein the coordinate system is based on the following equation:

$$V = P(\phi,\theta) + R*\text{Direction}(\phi,\theta)$$

where V is the corresponding point in thee-dimensional (3D) space to ($\phi,\theta$, r), P and Direction are vector functions expressed in terms of $\phi$ and $\theta$; and a function in the curved coordinate system to represent each tooth; and displaying the parametric representation of the teeth using the function and the coordinate system so as to provide a high-resolution image of the teeth.

2. The method of claim 1, further comprising storing a compact coordinate system description and the function in a file representing a compressed version of the digital data set.

3. The method of claim 2, further comprising transmitting the file to a remote computer.

4. The method of claim 3, further comprising displaying the computer model of the teeth using the function at the remote computer.

5. The method of claim 3, wherein the file is transmitted over a network.

6. The method of claim 5, wherein the network is a wide area network.

7. The method of claim 5, wherein the network is the Internet.

8. The method of claim 1, wherein the P and Direction functions are selected to minimize the deviation between the tooth model and a parametric surface specified by the curved coordinate system and the function.

9. The method of claim 1, wherein P and Direction are different for incisors and molars.

10. The method of claim 1, further comprising determining a radius value.

11. The method of claim 1, further comprising receiving an instruction from a human user to modify the graphical representation of the teeth and modifying the graphical representation in response to the instruction.

12. The method of claim 11, further comprising modifying the selected data set in response to the instruction from the user.

13. The method of claim 11, further comprising allowing a human user to select a tooth in the graphical representation and, in response, displaying information about the tooth.

14. The method of claim 11, wherein rendering the graphical representation comprises rendering the teeth at a selected one of multiple viewing orthodontic-specific viewing angles.

15. The method of claim 11, further comprising providing a user interface through which a human user can provide text-based comments after viewing the graphical representation of the teeth.

16. The method of claim 11, wherein rendering the graphical representation comprises downloading data to a remote computer at which a human view wishes to view the graphical representation.

17. The method of claim 1, further comprising delivering data representing the positions of the teeth at selected points along the treatment paths to an appliance fabrication system for use in fabricating at least one orthodontic appliance structured to move the teeth toward the final positions.

18. The method of claim 1, further comprising detecting teeth collision using the curved coordinate system.

* * * * *